US010953177B2

(12) United States Patent
Karlsson et al.

(10) Patent No.: US 10,953,177 B2
(45) Date of Patent: *Mar. 23, 2021

(54) ENDOTRACHEAL TUBE-INSERTING DEVICE

(71) Applicant: ALLYTEC AB, Solna (SE)

(72) Inventors: Annette Arnsäter Karlsson, Tenhult (SE); Måns Collner, Gränna (SE); Hannes Daniel Ulvegard, Jönköping (SE); Ronny Brakhya, Huskvarna (SE)

(73) Assignee: ALLYTEC AB, Solna (SE)

( * ) Notice: Subject to any disclaimer, the term of this patent is extended or adjusted under 35 U.S.C. 154(b) by 0 days.

This patent is subject to a terminal disclaimer.

(21) Appl. No.: 16/469,122

(22) PCT Filed: Dec. 13, 2017

(86) PCT No.: PCT/EP2017/082677
§ 371 (c)(1),
(2) Date: Jun. 12, 2019

(87) PCT Pub. No.: WO2018/109033
PCT Pub. Date: Jun. 21, 2018

(65) Prior Publication Data
US 2020/0023151 A1 Jan. 23, 2020

Related U.S. Application Data

(60) Provisional application No. 62/436,821, filed on Dec. 20, 2016.

(30) Foreign Application Priority Data

Dec. 14, 2016 (EP) ..................................... 16204087

(51) Int. Cl.
*A61M 16/04* (2006.01)
*A61M 25/01* (2006.01)

(52) U.S. Cl.
CPC ..... *A61M 16/0488* (2013.01); *A61M 25/0102* (2013.01); *A61M 25/0136* (2013.01); *A61M 2025/015* (2013.01)

(58) Field of Classification Search
CPC ..... A61M 16/0486–0497; A61M 16/04–0463; A61M 25/0102;
(Continued)

(56) References Cited

U.S. PATENT DOCUMENTS 5,016,614 A 5/1991 MacAllister
5,327,881 A 7/1994 Greene
(Continued)

FOREIGN PATENT DOCUMENTS

EP 1224904 A2 7/2002
EP 1803481 A2 7/2007
(Continued)

OTHER PUBLICATIONS

International Search Report and Written Opinion, Appl. No. PCT/EP2017/082677, dated Apr. 10, 2018.
(Continued)

*Primary Examiner* — Rachel T Sippel
(74) *Attorney, Agent, or Firm* — Winston & Strawn LLP

(57) ABSTRACT

An endotracheal tube-inserting device of the kind comprising a stylet part and a handle part for operating the stylet part is provided. The stylet part has a proximal stylet end part with a proximal stylet end and an opposite distal stylet end part with a distal stylet end; the proximal stylet end is situated at the handle part, and the distal stylet end has an extension in form of a bendable tip part with a free end; a tip part operating member includes at least a first string member and a second string member arranged along the length of at
(Continued)

least a length of the stylet part, and the handle part has an actuator means for operating at least the tip part operating member.

35 Claims, 18 Drawing Sheets

(58) Field of Classification Search
CPC . A61M 25/0133–0136; A61M 25/0141–0147; A61M 25/0152; A61M 2025/015; A61B 17/8819; A61B 1/01; A61B 17/01; A61B 1/267; A61B 1/0011; A61B 2017/0046; A61B 2017/00469; A61B 2017/00473; A61B 2017/22042
See application file for complete search history.

(56) References Cited

U.S. PATENT DOCUMENTS

| | | | |
|---|---|---|---|
| 6,539,942 B2 | 4/2003 | Schwartz et al. | |
| 8,382,665 B1 | 2/2013 | Fam | |
| 2002/0177750 A1 | 11/2002 | Pilvisto | |
| 2003/0024532 A1 | 2/2003 | Sniadach | |
| 2007/0156116 A1* | 7/2007 | Gonzalez | A61M 25/0136 604/528 |
| 2009/0064999 A1* | 3/2009 | Marten | A61M 16/0465 128/200.26 |
| 2013/0035548 A1* | 2/2013 | Ianchulev | A61B 1/00052 600/120 |
| 2013/0245372 A1 | 9/2013 | Lo | |
| 2013/0255671 A1 | 10/2013 | Furman et al. | |
| 2015/0096556 A1 | 4/2015 | Marks | |
| 2017/0000990 A1* | 1/2017 | Gerrans | A61M 29/00 |
| 2017/0189652 A1* | 7/2017 | Loh | A61M 25/09025 |

FOREIGN PATENT DOCUMENTS

| | | |
|---|---|---|
| WO | WO2009026095 A1 | 2/2009 |
| WO | WO2011025297 A2 | 3/2011 |
| WO | WO2011119521 A1 | 9/2011 |

OTHER PUBLICATIONS

M. Chandler, Apparatus, "Tracheal Intubation and Sore Throat: a Mechanical Explanation", Anaesthesia, 2002, 57, pp. 155-161(Year 2002).

Rose DK, Cohen et al., The Airway Problems and Predictions in 18,500 Patients, Can Journal of Anaesthesia, 1994, 41 ( 5 ), PP. 372-383, (year 1994).

C.M . Burket et al., Airway Management After Failure to Intubate by Direct Laryngoscopy: Outcomes in a Large Teaching Hospital, Can Journal of Anaesthesia., 2005, 52 ( 6 ), pp. 634-640 (Year 2005).

* cited by examiner

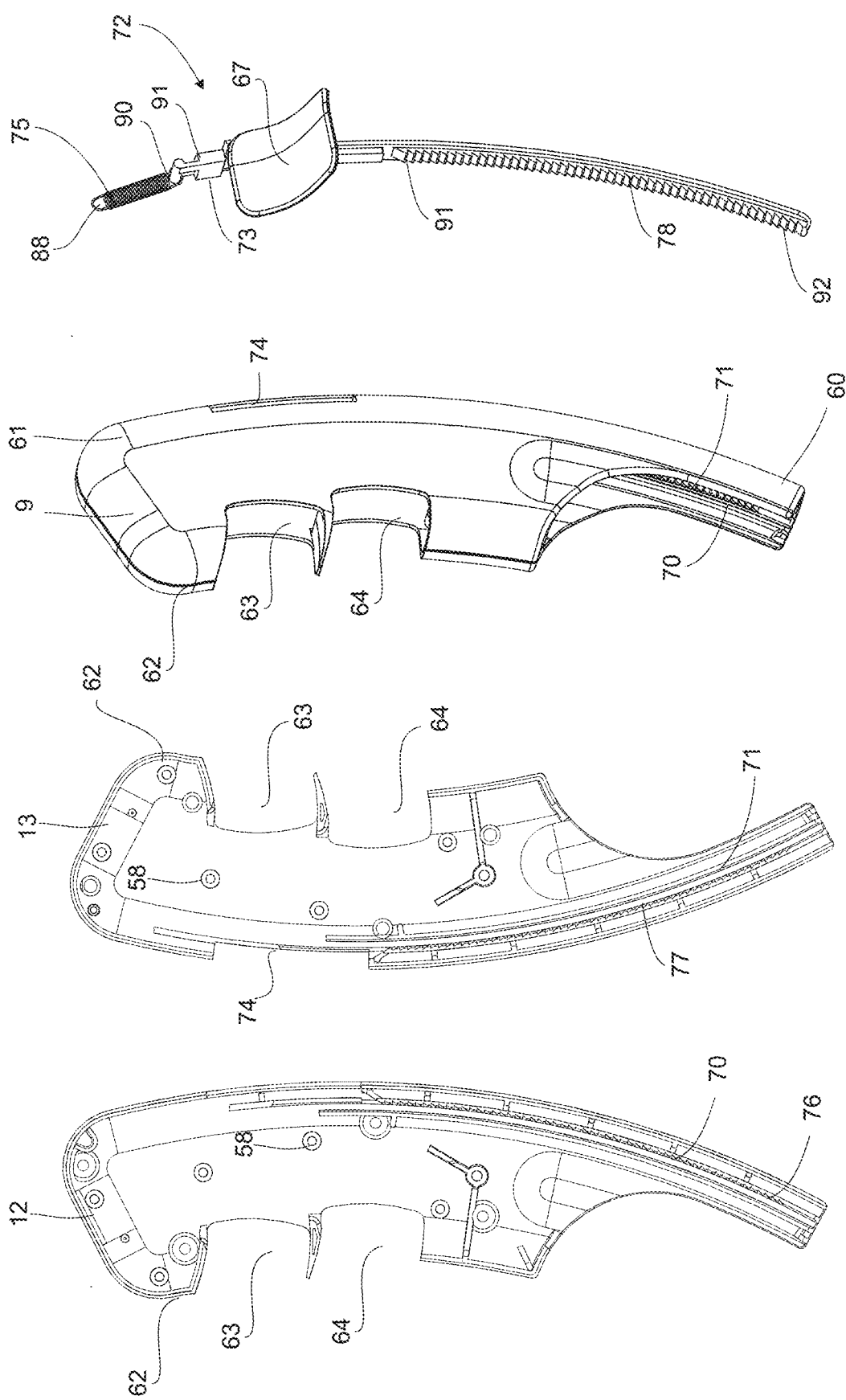

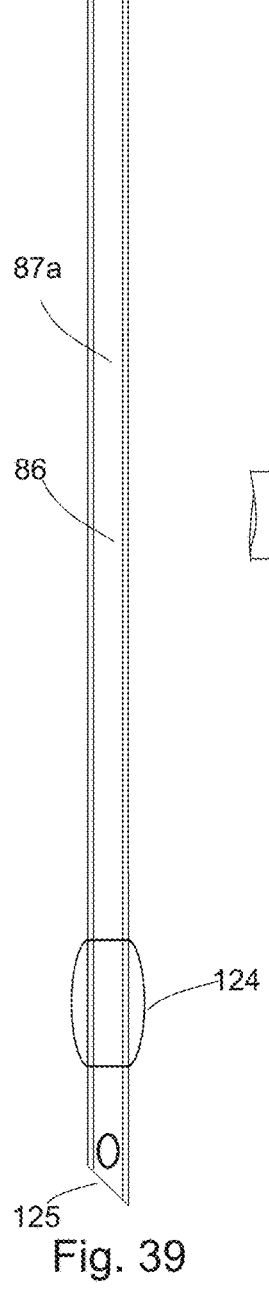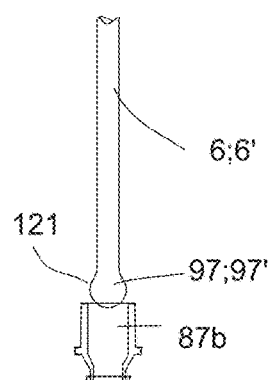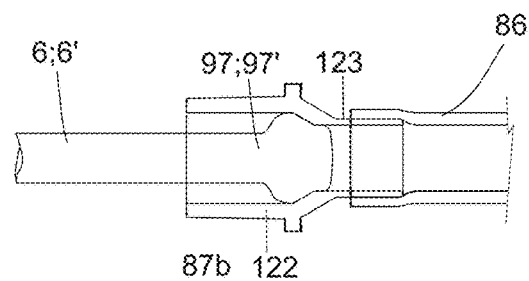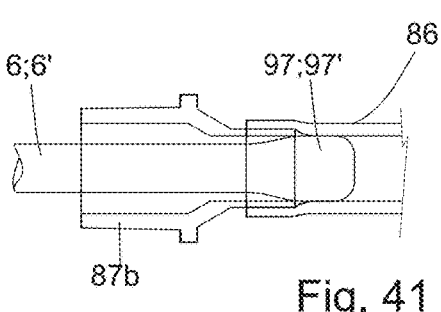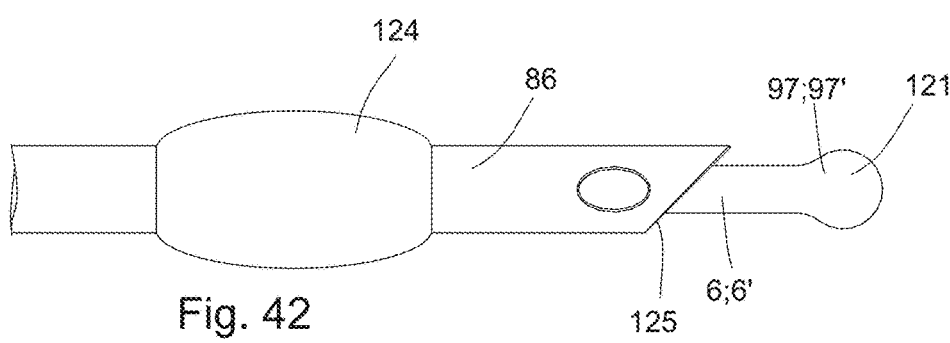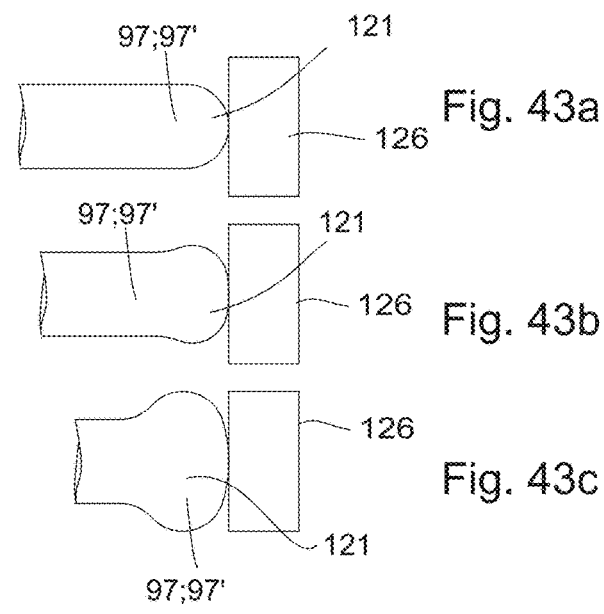

ENDOTRACHEAL TUBE-INSERTING DEVICE

This application is a 371 filing of International Patent Application PCT/EP2017/082677 filed Dec. 13, 2017, which claims the benefit of U.S. provisional application No. 62/436,821 filed Dec. 20, 2016 and claims priority to EP application No. 16204087.7 filed Dec. 14, 2016, the entire content of each which is expressly incorporated herein by reference thereto.

TECHNICAL FIELD

The present invention relates to an endotracheal tube-inserting device of the kind comprising a stylet part and a handle part for operating the stylet part, wherein the stylet part has a proximal stylet end part with a proximal stylet end and an opposite distal stylet end part with a distal stylet end; the proximal stylet end is situated at the handle part, and the distal stylet end has an extension in form of a bendable tip part with a free end; a tip part operating member includes at least a first string member and a second string member arranged along the length of at least a length of the stylet part, and the handle part has an actuator means for operating at least the tip part operating member.

In particular, the present invention relates to endotracheal intubation, and apparatuses and methods useful in the positioning of an endotracheal tube within the airways of a patient. The term "endotracheal tube-inserting device" used in the context of the present application means a device adapted for inserting an endotracheal tube into trachea. The "endotracheal tube-inserting device" is an intubator, thus a device for controlling, directing, and placing an intubation tube within the trachea.

BACKGROUND OF THE INVENTION

Unsuccessful direct laryngoscopy for orotracheal intubation occurs in particularly for patients having a "difficult airway". Failure incidence has been reported to be as high as 0.3% to 0.43% in the studies of Rose D K, Cohen M M. The airway: problems and predictions in 18,500 patients. *Can J Anaesth.* 1994; 41(5):372-383. doi: 10.1007/BF03009858, and of Burkle C M, Walsh M T, Harrison B A, Curry T B, Rose S H. Airway management after failure to intubate by direct laryngoscopy: outcomes in a large teaching hospital. *Can J Anaesth.* 2005; 52(6):634-640. doi: 10.1007/BF03015776.

Various kinds of blades and stylets are known in the art to improve the visuality of the airways when intubating a patient. Even though it may still be a huge challenge to help guide the tube into and along the patient's trachea, including lifting vallecula out of the way, trapping epiglottis to better expose the glottis and vocal cords.

Laryngoscopes are therefore often used to obtain a view of the glottis or the larynx, or to manipulate the tongue, glottis or larynx in order to facilitate insertion of such an endotracheal tube or other instruments such as endoscopes.

Even though airway-related complications associated with intubation procedures still occur. Examples of such complications include but are not limited to abrasion, hematoma, lacerations to lips, tongue, palate, pharynx, hypopharynx, larynx, and esophagus, injuries to lingual and/or hypoglossal nerve.

So despite the availability of various stylets and other implements, the insertion of endotracheal tubes can be difficult even for skilled physicians, particularly in patient's having anterior trachea and other conditions that make it challenging to guide the distal end of the endotracheal tube past the vocal cords and into the trachea.

As a tool to remedy at least some of the above side effects today widespread use is made of a video laryngoscope, such as a GlideScope® (Verathon, Inc., Bothell, Wash.), for real-time viewing a patient's airways during the intubation. This procedure has improved visuality of the airways significantly. Video laryngoscopes are however today used with rigid stylets, e.g. the GlideScope® is used with the GlideRite® Rigid Stylet that has a preformed rigid curvature. Other rigid stylets can be bend to a given preformed curvature but the tip has no individual maneuverability.

A typical conventional stylet contains a single flexible wire with a PVC coating and a uni-directional end cap that prevents the stylet from moving forward during the intubation process to lower the risk of unnecessary trauma to the patient. The stylet is inserted into the endotracheal tube so that the tube connector engages the uni-directional end cap.

U.S. Pat. No. 6,539,942 discloses a tubular endotracheal tube-inserting device capable of being flexed into a L-shape and through which a conventional imaging device, such as a nasopharyngoscope, is inserted centrally, so as to allow for direct visualization of the vocal cords US patent application no. 2013/255671 discloses an articulating stylet device having the ability to bend an endotracheal tube in more than one direction while the tube is being positioned in a patient's airway. This known articulating stylet device can bend the endotracheal tube in two directions, e.g. clockwise bend over a middle portion of the endotracheal tube and a counter-clockwise bend over a distal end portion of the endotracheal tube. This known articulating stylet is comprised of a plurality of beads arranged in sequential series. Each series is composed of differently configured beads having adjacent angled or beveled end surfaces. The beads have first and second longitudinal passageways for being threaded on a respective first and second metal wire, to make a stylet in form of a bendable "string of beads". One metal wire is secured to the free bead at the free distal end of the string of beads and the other metal wire is secured a distance from the first wire six beads proximal to the free distal bead. This different securing location of the first metal wire and the second metal wire makes the string of beads a separately articulating stylet device. This known stylet is given sufficient rigidity to keep elongate but bendable shape by keeping the beads intimately together on the metal wires, and has special tensioning means for that purpose. However, it is a challenge to arrange the bead correctly on the metal wires and a challenge to tension the wires correctly after all beads have been arranged as intended.

A major disadvantage of this known stylet is that the beads inevitably become slightly dislocated if tensioning of a wire is unsuccessful, or if the wire is too slack. The angled or beveled end surfaces of two adjacent beads need to be arranged in intimate contact to prevent jamming of the beads. If tensioning is lost the string of beads get too slack and cannot keep required dimensional shape to constitute a stylet for inserting an endotracheal tube, and if just a single bead becomes slightly offset or dislocated the string of bead cannot be bend as intended. A further huge disadvantage is that the gap between two adjacent beads may accidentally pinch and injure the endotracheal tube on the bead stylet, and dislocation of beads may increase stylet diameter and prevent its retraction from the endotracheal tube.

U.S. Pat. No. 5,327,881 relates to a fiberoptic intubating stylet, having a distal end that is able to be articulated in order to control the positioning of an endotracheal tube. The stylet is an elongate member that includes a first, semi-malleable portion at the proximal end thereof, a flexible region adjacent to the semi-malleable portion, and a distal end adjacent the flexible region. The distal end is rigid due to including or consisting of a lens device for facilitating viewing of objects. The rigid distal end with the lens extends into the flexible region, which is configured as a flexible bellow that can be manipulated by an articulation control assembly including control wires inside the stylet and extending from an attachment point at the distal end of the flexible region and terminating with control rings that are disposed outside of the stylet and the body. Thus the shape of the distal end part of the stylet cannot be altered during intubation, nor should it because then the lens cannot visualize as intended. Only the shape of the bellow can be altered to move the rigid distal end with the lens around. A further disadvantage is that once the semi-malleable portion and the flexible region has been bend to provide a curvature to the stylet, the bellow of the flexible region may hit against the interior wall of the endotracheal tube with the result that retraction of the stylet from the endotracheal tube cannot be done smoothly, and retraction is at the high risk that e.g. an expanded cuff of the inserted endotracheal tube dislocate, move to another location, and that air is supplied at an unintended location, or to a too low extent. Because the lens is situated at the distal stylet end such accidents will not be discovered before the patient gets difficulty in breathing.

SUMMARY OF THE INVENTION

It is a main aspect of the present invention to provide an alternative endotracheal tube-inserting device of the kind mentioned in the opening paragraph.

It is yet an aspect of the present invention to provide an endotracheal tube-inserting device of the kind mentioned in the opening paragraph by means of which an endotracheal tube can easier by positioned in a patient with a challenging anatomy than hitherto known.

It is yet an aspect of the present invention to provide an endotracheal tube-inserting device of the kind mentioned in the opening paragraph that has a stylet part with an improved ability to manipulate its free distal tip part.

It is yet an aspect of the present invention to provide an endotracheal tube-inserting device of the kind mentioned in the opening paragraph that has a stylet part with improved ability to independently bend different portions of a bendable tip part at the distal stylet end part.

It is yet an aspect of the present invention to provide an endotracheal tube-inserting device of the kind mentioned in the opening paragraph for use together with a video laryngoscope.

It is yet an aspect of the present invention to provide an endotracheal tube-inserting device of the kind mentioned in the opening paragraph wherein the stylet part is disposable.

It is yet an aspect of the present invention to provide an endotracheal tube-inserting device of the kind mentioned in the opening paragraph by means of which the risk of accidental insertion of an endotracheal tube in the esophagus is reduced significantly.

It is yet an aspect of the present invention to provide an endotracheal tube-inserting device of the kind mentioned in the opening paragraph by means of which the risk of accidental injuring the patient's airways during intubation is reduced.

It is yet an aspect of the present invention to provide an endotracheal tube-inserting device of the kind mentioned in the opening paragraph for use in an endotracheal procedure that is fast, efficient, and safe to the patient.

The novel and unique whereby these and other aspects are achieved according to the present invention consist in that
the first string member has a first proximal string end connected to a first string-operating member of the actuator means and an opposite first distal string end secured at a first string-securing location at the bendable tip part,
the second string member has a second proximal string end connected to a second string-operating member of the actuator means and an opposite second distal string end secured at a second string-securing location at the bendable tip part, which second string-securing location is different from the first string-securing location,
the stylet part comprises an elongate guide member that extends into the bendable tip part, which elongate guide member and bendable tip part lengthwise encases or supports at least a part of the first string member and at least a part of the second string member, and
the bendable tip part includes a tip-shaping member, and at least a distal part of said tip-shaping member is accommodated inside a flexible tubular cover.

Within the context of the present application the term "proximal" is used to indicate a position nearest to the handle part and the term "distal" is used to indicate a position nearest the bendable tip part. The term "housing" is used for a receptacle that is hollow to accommodate at least some of the mechanisms to operate the endotracheal tube-inserting device. The term "support" in context of the present application means that the elongate guide member "supports" the string members means that the string members runs close to the major part of the elongate guide member to guide said string members.

To conduct a typical laryngoscopic, orotracheal procedure the patient is first positioned so that the axial planes of the oral, pharyngeal and tracheal axes are aligned. The operator holds the laryngoscope, preferably a video laryngoscope, in his/her left hand. A cricoid pressure may be maintained, typically by another person assisting the operator, until the end of the procedure where the endotracheal tube is in correct place and the cuff has been inflated. The tip of the video laryngoscope is inserted into the right side of the patient's mouth and the blade is advanced to the base of the tongue, which is moved to the side, and the blade is moved forward. A straight blade is moved beneath the epiglottis and a curved blade is placed into the vallecula above the epiglottis keeping attention to keep the curved blade in midline and not applying traction along the axis of the laryngoscope handle as the laryngoscope lifts the tongue upwards away from the larynx to reveal the glottie opening and visualize the vocal cords. The endotracheal tube is then inserted through the vocal cords holding the stylet with the endotracheal tube with the right hand. An angled stylet may interfere with the passage of the endotracheal tube into the trachea and may cause difficult manipulation to pass through the vocal cords. Once the tip of endotracheal tube is past the vocal cords the stylet is removed, optionally the position of the endotracheal tube is corrected, the laryngoscope is removed, the cuff is inflated and safe insertion confirmed, e.g. by monitoring or observing end-tidal $CO_2$, listening using a stethoscope, observing condensation in the exterior length of the endotracheal tube, X-ray, etc. The skilled person knows these medical procedures.

Most known stylets for use in the above intubation procedures have a predetermined fixed curvature of both the elongate guide member and of the distal tip part at the beginning of the intubation. Thus the bendability is limited to bending into an overall final desired shape of the stylet part that cannot be altered during intubation rather than offering a distal tip part that is bendable on demand during intubation.

For the present invention two separate string members, a first string member and a second string member, respectively, are secured at two different securing locations inside the bendable tip part to arbitrarily move the bendable tip part at least lengthwise. When a string member of the tip part operating member is operated independent of the other string member of the tip part operating member, via the actuator means of the handle part, either by a string member being tensioned of by relaxing tensioning of a string member, the respective string-securing locations are moved in relation to the distal end of the elongate guide member, thus where said elongate guide member extends distally into the bendable tip part. Because the string members can be operated separately almost any imaginable shape of the distally arranged bendable tip part can be given to it simply by pulling the two string members more or less. One string member can be operated individually or both string members can be operated at the same time. Same or different levels of tensioning can be applied to the first string member and the second string member.

In the operating state of the endotracheal tube-inserting device the operator grasps around the handle part to operate the tip part operating member to almost arbitrarily move the first string member and/or the second string member lengthwise inside the elongate guide member to bend the bendable tip part at the distal stylet end. The free distal end of the bendable tip part can e.g. be moved below or above the elongate guide member, when seen in the operative orientation of the endotracheal tube-inserting device, to provide the bendable tip part with various kinds and degrees of e.g. S-shapes, mirror-shape C-shapes, L-shapes, or combinations of any of these shapes. Combinations of lateral offset and lengthwise offset first string-securing location and second string-securing location are within the scope of the present invention, and if the first string-securing location and the second string-securing location in addition to being lengthwise offset also are radially offset the bendable tip part can also move at least slightly to the side.

The bendable tip part includes a tubular cover that accommodates and protects the tip-shaping member to which tip-shaping member the first distal string end and the second distal string end are individually attached at the respective first string-securing location and second string-securing location. The tip-shaping member is part of the tip part operating member.

The elongate guide member and the bendable tip part safely sheath, guide, supports, keep and/or confine the first string member and the second string member so that the patient's tissue never can get in direct contact with any of said string members. Should the unimaginable accident occur that the first distal string end of the first string member disconnects from the first string-securing location and/or the second distal string end of the second string member disconnects from the second string-securing location such a detached end of a string member can never spring back to come in contact with patient's tissue and injure the patient. If the same happens for the beaded wire of the prior art stylet disclosed in US patent application no. 2013/255671 one or more beads could drop off the wire when the stylet is retracted from the endotracheal tube. Loose beads can in the best-case scenario be trapped inside the endotracheal tube in which case the procedure must be repeated, or worse, be trapped inside the airways, which could be fatal to the patient or require emergency surgery.

The tubular cover can e.g. be a soft plastic tube, e.g. of polyethylene or polyethylene vinyl chloride, but any material can be used provided that the tubular cover is able to yield and bend in response to bending of the tip-shaping member by pulling the string members inside the tubular cover without any noticeable increase in the overall diameter of the bendable tip part. If the plastic tube is transparent the operator can even visually follow how the tip-shaping member reacts in response to the operator operating the actuator means thereby providing the operator with a huge advantage of learning and obtaining knowledge of the induced impact on the tip-shaping member in response to such operating of the actuator means, and thus learn how to manipulate the tip-shaping member to assume any desired shape of the bendable tip part. Transparency is however in no way mandatory and same experience of shaping the tip-shaping member can be obtained irrespective of transparency by testing the actuator means.

The tip-shaping member and the tubular cover, that protectively surrounds at least the part of the tip-shaping member in extension of the elongate guide member, can be operatively secured to the elongate guide member in various ways, such as e.g. gluing, optionally also shrunken on the distal stylet end of the elongate guide member.

All or at least some of the components of the tip part operating member and of the actuation means can be at least partly hidden inside an appropriate respective receptacle, whether it being the handle part, the tubular cover, or the elongate guide member, which makes the overall design very hygienic and simple to sterilize in case of being intended for reuse.

The tip-shaping member has a first end and an opposite second end. Optionally the first end of the tip-shaping member of the tip part operating member can have a first end secured to or at the free distal tip of the bendable tip part, and/or the opposite second end can be confined inside the distal stylet end with or without actually being secured to the distal stylet end. In an alternative embodiment the first end of the tip-shaping member is not secured to the tubular cover at the free distal tip of the bendable tip part, but is restricted from being pulled back and turn around due to its trapping inside a close-fitting tubular cover, and due to the second end of the tip-shaping member being secured, e.g. inside or outside the elongate guide member or to the tubular cover.

The tip-shaping member can advantageously be of the kind adapted to return to a relaxed start shape when the actuation means is relaxed, thus adapted to instantaneously return, to the extent possible, to a given relaxed start shape once a deformation force applied to the tip-shaping member by either an operator or the patient's anatomy is relieved. Such returning may be an inherent property of the tip-shaping member, e.g. due to choice of material and/or due to having been given a shape with a memory prior to being inserted into the tubular cover. Thus due to the nature and properties of a.o. the tip-shaping member the bendable tip part is of the kind that can be deformed to various shapes and to various degrees by tensioning and relaxing the string members of the tip part operation member thereby altering the shape of said bendable tip part. The first string-operating member and the second string-operating member can be actuated arbitrarily and independent of each other in order to make the bendable tip part follow and conform to the anatomy of a patient during intubation. Once the tension at the string members are relieved the tip-shaping member will inherently attempt to assume its non-deformed shape to the extent possible. Thus when the bendable tip part is still inside the patient, it adapts its shape to the patient's anatomy at the insertion site, so the patient's anatomy defines the shape of the bendable tip part even if the tension at the string members are relieved. The anatomic constrictions and passages of the patient's airways prevents the bendable tip part from returning fully to its starting position, however once the bendable tip part is retracted fully from the patient the deformation is automatically reversed because the tip-shaping member always strive to attain the least tensioned configuration.

The tip-shaping member may include an elongate spring member, to confer the desired springiness for bending the tip-shaping member, and for remembering initial shape.

In one embodiment the elongate spring member of the tip-shaping member may include at least one elongate plate spring member, however the tip-shaping member may if advantageous to improve control of bending properties from the remote location of the string-operating members at the handle part, include at least two, optionally at least three, elongate plate springs arranged at least partly overlapping each other. The plate spring may have rectangular or square cross-sections, however, other cross-sections are within the scope of the present invention. Such other cross-sections could be oval, lens-shaped or circular.

Within the context of the present invention the term "plate spring" means an elongate flat component, preferably a strip, of spring steel material. Several plate springs in partly overlapping relationship provide an elongate spring member that has different stiffness along its length. By using partly overlapping plate springs for the elongate spring member the bendability of said elongate spring member along its length can be customized and targeted for the bendable tip part to be inclined to assume certain various shapes. A tip-shaping member composed of several partly overlapping plate springs may have a first end and an opposite second end consisting of just one single layer of plate spring be more resilient, flexible and bendable than where plate springs overlap. At the overlapping plate springs the tip-shaping member is more rigid and less inclined to bend. The different thickness of the tip-shaping member along its length makes encourages the tip-shaping member to achieve the different bending radii and positions along its length.

A similar structure of a tip-shaping member having different stiffness along its length due to different thicknesses of said tip-shaping member along its length can be manufactured of a single piece of material, e.g. spring steel or a dimensional stable plastic material that can be deformed to assume various shapes of the bendable tip-shaping member. Such manufacturing may include using appropriate processing steps such as molding, tooling, cutting, etc. Yet an option is to provide the tip-shaping member with different surface structure and topography along its length, such as undulations with different frequency at different lengthwise sections.

The tip-shaping member may include at least one pulley wheel having an axle fixed to said tip-shaping member at a string-securing location or fixed to the distal stylet end of the elongate guide member. The first string member and/or the second string member run along the circumference of the at least one pulley wheel, e.g. in a groove, to drive the at least one pulley wheel, thereby advantageously reducing the force needed to actuate the string-operating members and gaining a mechanical advantage. The term "mechanical advantage" is to be understood in its common technical understanding as a measure of force amplification, in the present context including using the string members and the pulley wheels, whereby forces applied to the string members by actuating the string-operating members, trades off forces against movement to obtain a desired amplification in the bending force on the tip-shaping member.

The bigger the mechanical advantage, the less force needs to be applied to the string-operating members, so by maximizing the length of a string member that extends from a string-operating member to a pulley wheel the actuation force needed to bend the bendable tip part is reduced whereby the operator much easier, faster and with less effort can provide the bendable tip part with a certain shape and change the shape on demand and "ad hoc".

The at least one pulley wheel may comprise a distal pulley wheel provided on a first side of the at least one plate spring at a first pulley wheel location at the free distal end of the bendable tip part, a proximal pulley wheel provided on a second side of the at least one plate spring opposite the first side at a second pulley wheel location spaced apart from the first pulley wheel location, a distal intermediate pulley wheel and a proximal intermediate pulley wheel provided adjacent each other on opposite sides of the at least one plate spring at an intermediate pulley wheel location between the first pulley wheel location and the second pulley wheel location. The at least one plate spring may pass between the distal intermediate pulley wheel and the proximal intermediate pulley wheel so that the distal intermediate pulley wheel can be provided on the first side of the at least one plate spring and the proximal intermediate pulley wheel be provided on the second side of the at least one plate spring.

When a force is applied to a string member the pulley wheels are pulled towards each other thereby bending the bendable tip part. The arrangement of the intermediate pulley wheels establishes a fixed pivot point or a fixed pivot location where the tip-shaping member tend to make a bending contributing to the bendable tip part being easily bend into shape during intubation.

In an embodiment of a bendable tip part with the above-mentioned four pulley wheels the first string-securing location may for example be at the proximal intermediate pulley wheel location and the second string-securing location be at the first pulley wheel location. In this case the second distal string end can be secured to the distal pulley wheel so that the second string member runs around the distal pulley wheel and the distal intermediate pulley wheel. Similarly, the first distal string end can be secured to the proximal intermediate pulley wheel so that the first string member runs around the proximal intermediate pulley wheel and the proximal pulley wheel. This way the string members can be lengthened by e.g. 2 times the distance between the pulley wheels which they run around thereby contributing to the mechanical advantage to make it easy to operate the respective string-operating member.

At least a part of the first string member and at least a part of the second string member may runs inside a common lumen of the elongate guide member to be protected inside said lumen, or run alongside a solid elongate guide member either just protected by the endotracheal tube or by being in confined alignment with at least a proximal length of the solid elongate guide member, e.g. running inside a respective recess in the solid elongate guide member, and being protected by a long flexible tubular cover extended to also cover said string members along the solid elongate guide member.

The exterior face of the tubular cover may be selected having a coefficient of friction that is lower than the coefficient of friction of an endotracheal tube to be mounted on the endotracheal tube-inserting device so that the endotracheal tube can be mounted and demounted the endotracheal tube-inserting device without sticking to said endotracheal tube-inserting device.

The handle part may advantageously comprise a housing for accommodating and protecting components of the endotracheal tube-inserting device, such as at least some of a proximal stylet end part, a proximal end of the string members, a tube ejecting mechanism, and at least a part of the actuation means. The housing may have various shapes depending on the configuration of said components. An ergonomic, easy graspable and maneuverable shape of the handle part may be preferred. In one embodiment the elongate guide member can be a curved pipe inside which at least a part of the string members is guided and accommodated.

The proximal stylet end part, the distal stylet end part and the bendable tip part may have same of different initial curvatures. The choice of appropriate same or different initial curvatures may depend on the length of said parts and be selected in view of reducing wobbling during use. Said curvatures may also depend on the design of the housing and of the position and configuration of the string-operating members on or in relation to the housing.

In one embodiment the stylet part can have a first center of curvature above said stylet part, and the pre-shaped bendable tip part have a second center of curvature on the same side of the endotracheal tube-inserting device thereby providing a device with an overall C-shape. In this embodiment both the stylet part and the bendable tip part follow a concave function and both the first and the second centers of curvature are above the bendable tip part and above the proximal stylet end part, and on the side of the endotracheal tube-inserting device facing away from the patient when the endotracheal tube is just guided in position intubation. In this embodiment of an endotracheal tube-inserting device the handle part is turned away from the patient's head when inserting the distal tip part into trachea thereby allowing the operator to operate the device well free of the video laryngoscope with distance to the patient. However, some operators experience this distance as being too long and that they need to reach too far above the patient to have proper control of the endotracheal tube-inserting device during intubation, and that maneuvering of the distal tip part by means of the string-operating members become rather strenuous and difficult.

The centers of curvature are in an alternative embodiment of an endotracheal tube-inserting device located on opposites sides of the endotracheal tube-inserting device along its length. The stylet end part may follow a concave function and extend into the pre-shaped bendable tip part that follows a convex function to provide a device with an overall S-shape, that are very easy to grasp and maneuver. When this embodiment of an endotracheal tube-inserting device is inserted via the patient's mouth the stylet part curves towards the patient face. In this alternative embodiment at least the proximal stylet end part can have a first center of curvature below the stylet part and the distal stylet end part have a second center of curvature on the opposite side, thus above the bendable tip part when the endotracheal tube is just guided in position intubation.

In order to adapt to the curvature of the proximal stylet end part the housing may curve the same way as said proximal stylet end part of the elongate guide member.

The housing can e.g. be a curved tubular body having a circumferential exterior wall that encases several of the components of the endotracheal tube-inserting device needed for its operation. The tubular body offers a good grip for holding on to the endotracheal tube-inserting device during it.

Preferably the elongate guide member can have a curvature following a sector of a circle or have curved sections of different curvatures. E.g. the proximal end part of the elongate guide member may be defined by a first sector of a circle having a large first radius. This proximal end part may extend via an intermediate part defined by a second sector of a circle having a second radius smaller than the first radius, which intermediate part then again may extend into the distal end part of the elongate guide member, which distal end part can have a third radius smaller than the second radius. This design is just given as an example of a suitable curvature design of the elongate guide member and variations are indeed feasible within the scope of the present invention. Preferred curvature(s) of the elongate guide member may be the curvature(s) that conforms, at least to some extent, to the shape of the airway with the patient's head held in the neutral position, a curvature often referred to as the "the Magill Curve". "A Magill Curve" having a radius of curvature of 140 mm±20 mm is found to be about optimum for the average airway, [Tracheal intubation and sore throat: A mechanical explanation; M. Chandler; *Anaesthesia,* 2002, 57, pages 155-161], and suited for the present invention, although various curvatures may work better for various target patients.

The elongate guide member can e.g. be made of aluminum or similar lightweight material. Alternatively, the elongate guide member is made of plastic. The elongate guide member may be form-stable, thus not malleable, although malleable elongate guide members are not excluded within the scope of the present invention.

The first string-securing location and the second string-securing location can be situated lengthwise offset to facilitate bending of the bendable tip part in a more or less distinct S-shape, mirror S-shape, L-shape or C-shape to assume a shape that can navigate the least obstructed into trachea and be made straight again if and when desired and needed, e.g. for retracting the stylet part, e.g. retracting the stylet part from an endotracheal tube that was sheathed on the stylet part prior to the introduction of the endotracheal tube-inserting device into trachea and now is left as introduced for ventilation of the patient.

Bending and relaxing the bendable tip part can take place both during inserting the bendable tip part with or without an endotracheal tube sheathed on the stylet part as well as when the endotracheal tube-inserting device is retracted.

Emphasis is made that for some patients it may suffice that just one of the first string member and the second string member is operated for the bendable tip part to assume a shape suited for easy passing the endotracheal tube-inserting device past the glottis and between the vocal cords.

For difficult airways it is however highly beneficial that the endotracheal tube-inserting device of the present invention is provided with the ability to arbitrarily control and customize the shape and curvature of the bendable tip part to a shape specific for the airway anatomy of a certain patient, which significantly eases the insertion of both the stylet part and an endotracheal tube sheathed on the stylet part.

If the first string-securing location and the second string-securing location are also radially or laterally offset each other the bendable tip part can also be moved slightly from side to side. So in one embodiment the first string-securing location and the second string-securing location may be both radially/laterally and lengthwise offset so that both bending the bendable tip part lengthwise and moving a securing location slightly to the side are possible.

The above-mentioned improved and very versatile in situ and real time ability to change the shape of the bendable tip part both outside and inside the patient's body provides an endotracheal tube-inserting device that is very fast and convenient to operate, insert correct, and retract without injuring or otherwise harming the patient. The string-securing locations can be moved into a plurality of different positions so that the shape of the bendable tip part can be adapted for use with even the most difficult airways thereby making the endotracheal tube-inserting device of the present invention not only user-friendly but also patient-friendly.

The tip-shaping member may have a first end secured to the free end of the bendable tip part, e.g. to the tubular cover, and an opposite second end secured to or at the vicinity of the distal end of the elongate guide member so that the tip-shaping member is kept from coiling inside its accommodation in the tubular cover of the bendable tip part, and so that when the first string-securing location and the second string-securing location is tensioned and/or relaxed the first end and the second end of the tip-shaping member are firmly attached at the respective securing points associated with the bendable tip part and/or the stylet part and does not displace lengthwise inside the tubular cover. The handle part incorporates the actuator means adapted to operate the tip part operating member to bend the bendable tip part of the stylet part.

In an advantageous embodiment the first string-operating member of the actuator means may include a first lever body pivotably arranged about a first pivot axis, which preferably is located inside the handle part, and the second string-operating member may include a second lever body pivotably arranged about a second pivot axis, which preferably also is located inside the handle part, said first lever body may have at least one first actuator lever arm extending from the first pivot axis to a first actuator, and an at least one opposite first string-operating lever arm to which the first proximal string end is operatively connected to change the position of the first distal string end relative to at least the distal stylet end in response to actuating the first actuator, said second lever body may have at least one second actuator lever arm extending from the second pivot axis to a second actuator, and at least one opposite second string-operating lever arm to which the second proximal string end is secured to change the position of the second distal string end relative to at least the distal stylet end in response to actuating the second actuator.

Depressing the first actuator then makes the at least one first actuator lever arm to pivot about the first pivot axis whereby the first string-operating lever arm pulls the first proximal string end away from the proximal stylet end inside the housing and bends the bendable tip part by retracting the first distal string end towards the distal stylet end. Similarly, depressing the second actuator makes the at least one second actuator lever arm to pivot about the second pivot axis whereby the second string-operating lever arm pulls the second proximal string end away from the proximal stylet end and bends the bendable tip part by retracting the second distal string end towards the distal stylet end inside the housing. A first fulcrum is defined at the first pivot axis and a second fulcrum is defined at the second pivot axis.

The at least one first actuator lever arm extends as the effort arm and the first string-operating lever arm extends as the resistance arm on opposite sides of the first fulcrum. Upon application of a force to the first actuator at the free end of the first actuator lever arm the first string-operating lever arm pivots about the first pivot axis of the first fulcrum whereby the first string member is pulled backwards away from the proximal stylet end thereby also pulling the first distal string end closer to the proximal stylet end. When the force on the first actuator is relieved the first lever body returns to its starting position, but can be in any pivoted position between the starting position and the ultimate pivoted position depending amongst other on an adjustment of the level of force applied to the first actuator.

Similarly, the at least one second actuator lever arm extends as the effort arm and the second string-operating lever arm extends as the resistance arm on opposite sides of the second fulcrum. Upon application of a force to the second actuator at the free end of the second actuator lever arm the second string-operating lever arm pivots about the second pivot axis of the second fulcrum whereby the second string member is pulled backwards away from the proximal stylet end thereby also pulling the second distal string end closer to the proximal stylet end. When the force on the second actuator is relieved the second lever body returns to its starting position, but can be in any pivoted position between the starting position and the ultimate pivoted position depending on an adjustment of the level of force applied to the second actuator.

In an embodiment wherein the second string-securing location is different from the first string-securing location, application of various levels of force to one or both of the first actuator and the second actuator of the actuator means will induce bending of the bendable tip part in response to operating the first actuator and the second actuator.

The handle part may comprise that the housing accommodates at least the first lever body and the second lever body, which housing has a first opening for making the first actuator accessible to pivot the first lever body from outside the housing, and a second opening for making the second actuator accessible to pivot the second lever body from outside the housing.

The pivoting of the first level body and the second level body may reach their respective ultimate positions when hitting a stop provided at the handle part, e.g. inside the housing of the handle part, optionally simply hitting the inside of the housing. The first actuator and the second actuator are both accessible for the operator via such a housing, e.g. via the respective first opening and the second opening in the housing above the respective pivot axes when the handle part are grasped by a hand in the operation position. Preferably the first actuator and the second actuator protrude from the respective first opening and second opening.

Preferably the first lever body may be pivotably suspended to move a first string-securing member of the housing, and the second lever body may be pivotably suspended to move a second string-securing member of the housing, and wherein the first string-securing member may be arranged spaced from the first pivot axis to allow the first lever body to pivot and pull at the first string member. Similarly, the second string-securing member may be arranged spaced from the second pivot axis to allow the second lever body to pivot and pull at the second string member. A string-securing member can be any kind of structure suited to be secured to the corresponding lever body to pivot said lever body about its pivot axis. An example of a string-securing member includes but are not limited to a pin fitting into a cavity provided at the free end of a string-operating lever arm opposite the associated pivot axis or being hooked to this location, and where the string member is secured to the pin e.g. by being wound on the pin to be firmly secured. Other examples are other female securing means provided in or at the free end of a string-operating lever arm, e.g. a hole, an eye or a ring for tying the string member at the proximal string end.

The above embodiment of an endotracheal tube-inserting device may further include that
  a suspension body are arranged inside the housing and being configured with the first pivot axis and the second pivot axis for pivotally suspending the first lever body and the second lever body, respectively,
  that the first proximal string end is operatively connected to the end of the first string-operating lever arm opposite the first pivot axis to displace the first string member along the elongate guide member,
  that the second proximal string end is operatively connected to the end of the second string-operating lever arm opposite the second pivot axis to displace the second string member along the elongate guide member, and wherein
  the first string-securing member and the second string-securing member are arranged below the suspension body opposite the respective first actuator and second actuator.

Because an actuator is located remote from a string-securing member this design and suspension of lever bodies provide for maximum force application at minimum depression of the corresponding actuator. The first lever body and the second lever body can be operated individually by said spaced apart respective first and second actuators, the first lever body can be operated and pivoted unobstructed of the pivoting of the second lever body, even during this second lever body also being operated.

In an embodiment of the present invention the first lever body can be a first bifurcated lever body having opposite first legs joined by the first actuator, which opposite first legs extends from the first actuator into opposite first actuator lever arms that extends further via the first pivot axis into opposite first string-operating lever arms, and the second lever body can be a second bifurcated lever body having opposite second legs joined by the second actuator, which opposite second legs extends from the second actuator into opposite second actuator lever arms that extends further via the second pivot axis into opposite second string-operating lever arms.

The first bifurcated lever body thereby defines, in-between the opposite first legs, a first gap for receiving a first part of the suspension body and for pivotally suspending the first lever body to the first pivot axis. A force on the first actuator can then pivot the first lever body between its ultimate depressed position, wherein the first actuator, that bridges the opposite first legs, hits on the suspension body to stop further pivoting, and a relaxed start position, wherein there is a gap between the bridging first actuator and the suspension body to allow depression of the first actuator.

Similarly, the second bifurcated lever body thereby defines, in-between the opposite second legs, a second gap for receiving a second part of the suspension body and for pivotally suspending the second lever body to the second pivot axis. A force on the second actuator can then pivot the second lever body between its ultimate depressed position, wherein the second actuator, that bridges the opposite second legs, hits on the suspension body to stop further pivoting, and a relaxed start position, wherein there is a gap between the bridging second actuator and the suspension body to allow depression of the second actuator.

The ultimate depressed positions of an actuator can also be when the legs hit a component of the housing or the housing itself, in which cases the bridging part of an actuator may even not be able to move into contact with the suspension body.

The first part of the suspension body may e.g. be the part of the suspension body closest to the proximal stylet end and the second part of the suspension body may e.g. be the part of the suspension body farthest from the proximal stylet end.

The suspension body may function to suspend the lever bodies spaced apart from each other so that they can pivot smoothly without hitting each other.

So when a lever body is pivoted by depressing the corresponding actuator the end of the corresponding string-operating lever arm, which is connected to the string-securing member, can pull or relax a string member without the string members get entangled, jam, or the lever bodies hit on each other.

In an alternative embodiment of the present invention the first string-operating member and the second string-operating member can be hinged to an tubular exterior wall of a curved tubular body that define a housing to pivot between a relaxed position wherein any of the first string-operating member and the second string-operating member protrude spaced from the tubular exterior wall and an actuated position wherein the first string-operating member and the second string-operating member are closer to the tubular exterior wall than in the relaxed position. The tubular body is convenient to grasp to operate the first string-operating member and the second string-operating member, which first string-operating member and the second string-operating member expediently may be arranged adjacent each other to be operated by adjacent fingers of the hand used to grasp on the tubular body that are part of the handle part.

The first string-operating member and the second string-operating member can for example simply be pivotable flaps, such as a pivotable first flap to which the first proximal string end of the first string member is secured, and a pivotable second flap to which the second proximal string end of the second string member is secured.

Said flaps may preferably be curved flaps having same center of curvature as a cross-section as the exterior tubular wall, however other curvatures are within the scope of the present invention. The curved flaps can for example be provided by a cross-sectional segment of the exterior tubular wall, in which embodiment the curved flaps extend pivotably by its attachment of a single flap edge at the joining to the exterior tubular wall, the edge being the hinge, as an integral part of said tubular wall. The hinge may have e.g. a weakening, indent of similar feature that facilitates and promotes the pivoting of the flap. The flaps can also be hinged to the exterior tubular wall by means of another kind of hinge, such as a leaf hinge. Other kinds of flaps, curved or straight, can be secured to the exterior tubular wall as separate objects. In the relaxed condition of the string members, said string members can either pass into the interior of the tubular body via a respective string hole made for this entry purpose, or span the somewhat larger hole left when the flaps are excised form the exterior tubular wall and run outside the exterior tubular wall before it enters the lumen of the tubular body at the vicinity of the proximal stylet end. So the string members can be guided on the outside of tubular exterior wall and be secured to the respective pivotable flaps.

In yet an embodiment of string-operating members the first string-operating member and the second string-operating member may be constituted of opposite lever arms of a rocker having its fulcrum at the tubular exterior wall and the string members respectively secured to said lever arms.

Combinations of the afore-mentioned features amongst and within the embodiments are within the scope of the present invention. In particular, the invention foresees the combination of different kinds of tip-shaping members with different kinds of string-operating members, how said string-operating members are hinged and/or pivot and move the string members, how the string members extends in relation to the handle part, and in particular in relation to the tubular body.

Irrespective of the string-operating members are actuator button, flaps, or rockers they preferably are connected to the respective string members in a manner that makes the string-operating members automatically jump back into a relaxed position once any force applied to said string-operating members are relieved. Thus the string-operating members may have an inherent springiness provided, amongst others, by the way the string-operating members are connected to the housing combined with the length and locations of the string members, but the provision of a spring for promoting return to its relaxed condition of a string-operating member that has been subjected to a force is not excluded by the present invention.

Preferably the proximal stylet end of the guide member is located inside the housing to provide a solid anchoring of the stylet part and reduce overall length of the endotracheal tube-inserting device.

The free distal tip at the end of the distal tip part may have a larger cross-section than the tubular cover along the length of the bendable tip part. In order to make it easy to push the endotracheal tube onto an endotracheal tube-inserting device having an enlarged free distal tip and off the endotracheal tube-inserting device again the free distal tip at the end of the distal tip part may advantageously be soft and flexible. The free distal tip may preferably be so soft that it automatically forms into a large contact area when pushed against an obstacle, so that the free distal tip cannot damage sensitive tissue at a given force acting on the tissue when the endotracheal tube-inserting device is being forced forward into trachea. The softness of the free distal tip can be adjusted by choice of material and/or by way of design and shape, including by selecting a certain wall thickness or graduation of said wall thickness.

The shape of the free distal tip can be round or drop-shaped optionally having a larger diameter than the exterior diameter of the elongate guide member or of the interior diameter of the endotracheal tube used with the endotracheal tube-inserting device.

For use in endotracheal intubation an endotracheal tube may advantageously be provided on the stylet part. The nature and curvature of the endotracheal tube, if not straight and pliable, may optionally be of the kind that conforms to or has the same curvature as the curvature of the elongate guide member of the stylet part, thereby also conforming to the shape of the airway, as in the position wherein the patient's head is held in the neutral position, as described above.

The endotracheal tube suited for the present endotracheal tube-inserting device may e.g. have a standardized airway connector of internal diameters of e.g. 15 mm and 22 mm, thus conforming to ISO standard no. 5356-1, so that it by way of its standardization also can be connected to all other airway equipment. Situations with non-compatibility between coupling of airway equipment and endotracheal tube, and urgent need for special adaptors to establish ventilation, are thus prevented.

A conical tube connector may be arranged on the stylet part at the proximal stylet end part to mate with the airway connector of the endotracheal tube, so that the endotracheal tube stay put and correct on the stylet part when the endotracheal tube-inserting device is moved into the airways. The conical shape of the tube connector allows the tube connector to fit together with airway connectors of different diameters. A large diameter tube connector is just moved closer upwards towards the handle part to couple around the conical tube connector than needed for a smaller diameter tube connector. There are different lengths of endotracheal tubes and therefore the position of the conical tube connector on the stylet part may in some embodiments be made adjustable, e.g. by allowing the conical tube connector to slide on the elongate guide member.

The endotracheal tube may, or may not, have a cuff which can be inflated to seal the lungs against the liquid secretions present in the upper airway, and seal distally to allow ventilation of the patient under controlled pressure and defined gas mixture. Use of an endotracheal tube with inflatable cuff is almost always used for adults whereas most pediatric tubes are uncuffed.

The endotracheal tube-inserting device of the present invention may be used with both an uncuffed endotracheal tube and a cuffed endotracheal tube. The size of the appropriate endotracheal tube depends on e.g. the patients age and airway anatomy size. If a cuffed endotracheal tube is used the internal diameter in millimeters is typically calculated as 4+(Age/4). In case of a cuffed endotracheal tube the size of its internal diameter is typically calculated as 3.5+(Age/4). Such endotracheal tubes may however have standard airway connectors that allow the same endotracheal tube-inserting device to be used with several different endotracheal tubes.

Operation of the endotracheal tube-inserting device according to the present invention can be done with one and the same hand, without the hand needs to be taken off the handle part. Thus the endotracheal tube-inserting device can easily be held steady and be operated without huge motions of the hand holding and operating it, and without the need to change the position of the hand on the handle part at any time during the endotracheal procedure, without and without the operator needing to apply huge force and move his hand around on the handle part. The endotracheal tube-inserting device has a convenient size and shape of the handle part.

The string-operating members may be adapted to provide a tactile feed-back to the operator in response to applying a force on and/or relieving said force from the string-operating members.

In order to get the endotracheal tube off the stylet part, the endotracheal tube-inserting device may further have a tube ejecting mechanism.

An exemplary tube ejecting mechanism may comprise a ratchet mechanism and a reciprocating third actuator for operating the ratchet mechanism to stepwise move the tube connector and thus the endotracheal tube sheathed on the stylet part along the elongate guide member towards the distal stylet end.

The ratchet mechanism advantageously comprises a rack part extending along the length of the housing and a wedge part protruding from the tube connector to engage the rack part.

The rack part may have a first stationary rack part, a second stationary rack part, and a moveable third rack part arranged lengthwise between the first stationary rack part and the second stationary rack part, which moveable third rack part may have the third actuator arranged to protrude from the housing so as to be accessible for a user in a reciprocating manner from outside the housing. To allow the moveable third rack part to return to a starting position the proximal rack end of the moveable third rack part may be suspended to an interior face of the housing, or to another interior position of component of the handle part, by means of a spring. The spring can be stretched when the third actuator is moved lengthwise along the housing in order to displace the moveable third rack part between and along the lengths of the first stationary rack part and second stationary rack part. Due to the inertia applied to the stretched spring, the spring automatically returns to a more relaxed starting position once the force applied to the third actuator is relieved, thereby pulling the third actuator and the moveable third rack part back to the starting position, and thereby allowing repetition of a similar actuation of the moveable third actuator to displace the tube connector further towards the distal stylet end, and thereby also moving the endotracheal tube off the stylet part.

The wedge part may have a center wedge part that engages between the teeth of the moveable third rack part. The center wedge part may advantageously be located between opposite lateral wedge parts of the wedge part. In the context of the present invention the term "opposite lateral wedge parts" means that the two wedge parts extend on opposite sides of the center wedge part and thus on opposite longitudinal sides of the moveable third rack part.

The lateral wedge parts engage the teeth of the stationary first and second rack parts to keep the wedge part and the tube connector in the lengthwise forwarded position while the moveable rack part returns to its starting position to be able to repeat the step of actuating the moveable third actuator to move the wedge part and the tube connector further forward towards the distal stylet end. So the engagement between the lateral wedge parts and the teeth of the stationary rack keeps the tube connector in the moved-forward position wherefrom backwards movement is impossible due to the lateral wedge parts being trapped between the teeth of the stationary rack parts. The forward-angled teeth of the moveable third rack part however serve as the tool for every further forward movement of the wedge part until the teeth and center wedge part engage again closer to the distal stylet end until the endotracheal tube is moved so far down the trachea that the stylet part can be withdrawn without the endotracheal tube comes along.

So both the moveable third rack part, the first stationary rack part, and the second stationary rack part may have a plurality of teeth alternating with a plurality of grooves and extending crosswise the length of the respective rack part to catch an opposite facing part of a wedge part thereby, on the one hand preventing the wedge part from returning towards the housing, and on the other hand facilitating further forward movement of the wedge part. The teeth of the rack parts may conveniently be angled towards the proximal stylet end, and the grooves between said adjacent teeth be designed to mate with the center wedge part and the lateral edge parts of the wedge part, respectively. To ensure good engagement the wedge part may taper to a thin edge towards the multiplicity of teeth to lock between the teeth.

The housing can expediently also accommodate at least a part of the ejecting mechanism and be open distally to allow the moveable rack part and the wedge part with the tube connector to move along the length of the handle part.

BRIEF DESCRIPTION OF THE DRAWINGS

The invention will be explained in greater details below with reference to the drawing, which illustrates exemplary embodiments to disclose further advantageous and technical features and effects of the present invention.

FIG. 9 is a side view inside the first shell part of the housing of the first embodiment of an endotracheal tube-inserting device, FIG. 10 is a side view inside an associated second shell part, FIG. 11 is a perspective view of the shell parts in assembled state to achieve the housing of the first embodiment of an endotracheal tube-inserting device, FIG. 12 is a perspective view of a moveable third rack part of a tube ejecting mechanism, which third rack part is seen from a third actuator, FIGS. 39-43c illustrate a soft flexible free distal tip of a bendable tip part upon being inserted into the endotracheal tube via the tube's airway connector.

DETAILED DESCRIPTION OF SPECIFIC EMBODIMENTS

Figure 1:
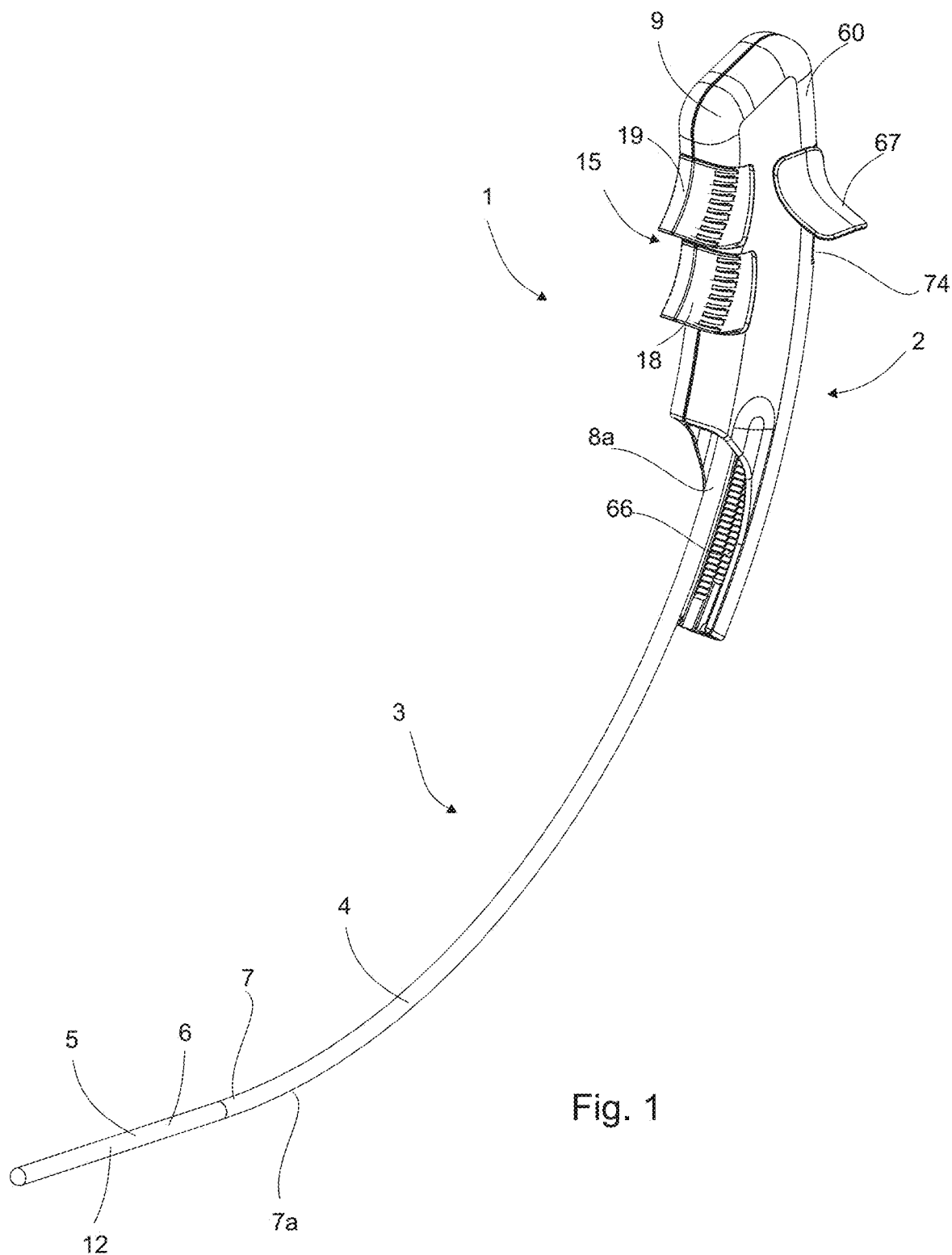
FIG. 1 is a perspective view of a first embodiment of an endotracheal tube-inserting device of the present invention seen oblique from the side and from the actuators.
Figure 2:
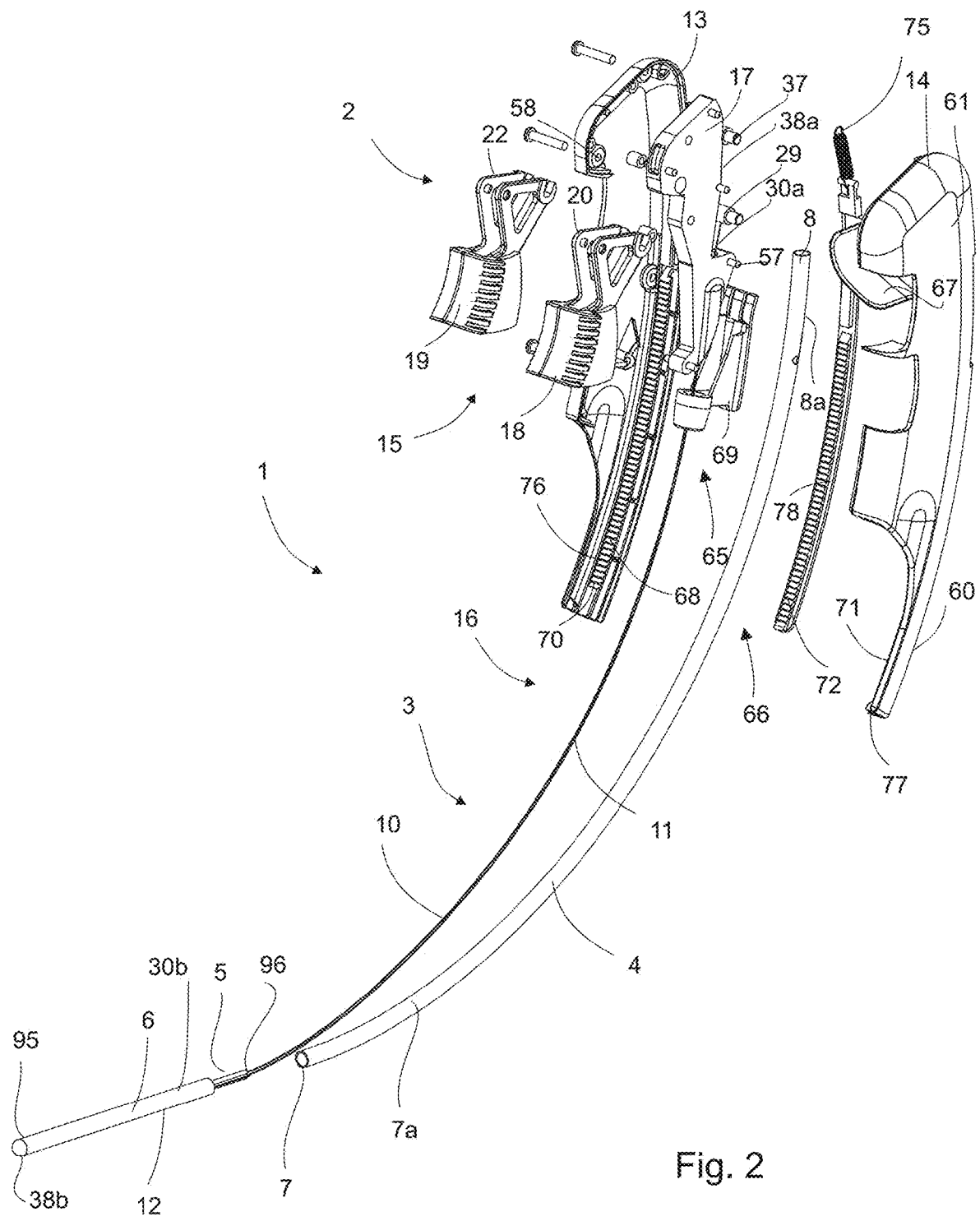
FIG. 2 shows the same in an exploded view.

A first embodiment of an endotracheal tube-inserting device 1 is seen in perspective view in FIG. 1, and in a perspective exploded view in FIG. 2.

The endotracheal tube-inserting device 1 comprises a handle part 2 and a stylet part 3. The stylet part 3 has an elongate guide member 4 that extends into a bendable tip part 6 at a distal stylet end 7 of a distal stylet end part 7a, and inside the handle part 2 at an opposite proximal stylet end part 8a that has a proximal stylet end 8. The handle part 2 defines a receptacle in form of a housing 9 that accommodates at least a part of a mechanism to bend the bendable tip part 6, and at least a part of a mechanism to eject from said stylet part 3 an endotracheal tube (not shown) sheathed on the stylet part 3. In the present exemplary embodiment of an endotracheal tube-inserting device 1 the elongate guide member 4 is shown to be a smoothly curved pipe, and the bendable tip part 6 is not transparent. The shown curvature of the elongate guide member 4 is an example and other curvatures, e.g. having larger or smaller radii, are foreseen within the scope of the present invention.

As seen best in FIG. 2 the mechanism to bend the bendable tip part 6 includes a first string member 10 and a second string member 11 extending inside the elongate guide member 4. The first string member 10 and the second string member 11 are both connected to a tip-shaping member 5 located at least partly inside a tubular cover 12 and having a first end 95 secured to the free distal tip 97 at the end 98 of the distal tip part 6 and an opposite second end 96 secured to the elongate guide member 4 or the stylet part 3. The tubular cover 12 and the tip-shaping member 5 are part of the bendable tip part 6.

The housing 9 has a first shell part 13 and an opposite second shell part 14 that, when assembled, provide a space for at least a part of an actuator means 15 for pulling and relaxing tensioning of the tip-shaping member 5 inside the tubular cover 12 by pulling and relaxing tensioning of the first string member 10 and the second string member 11, both of which are secured to said tip-shaping member 5 at different securing locations (not seen in FIG. 1 and FIG. 2) inside the tubular cover 12 of the bendable tip part 6.

A tip part operating member 16 thus includes at least the tip-shaping member 5, the first string member 10 and the second string member 11.

Figure 3:
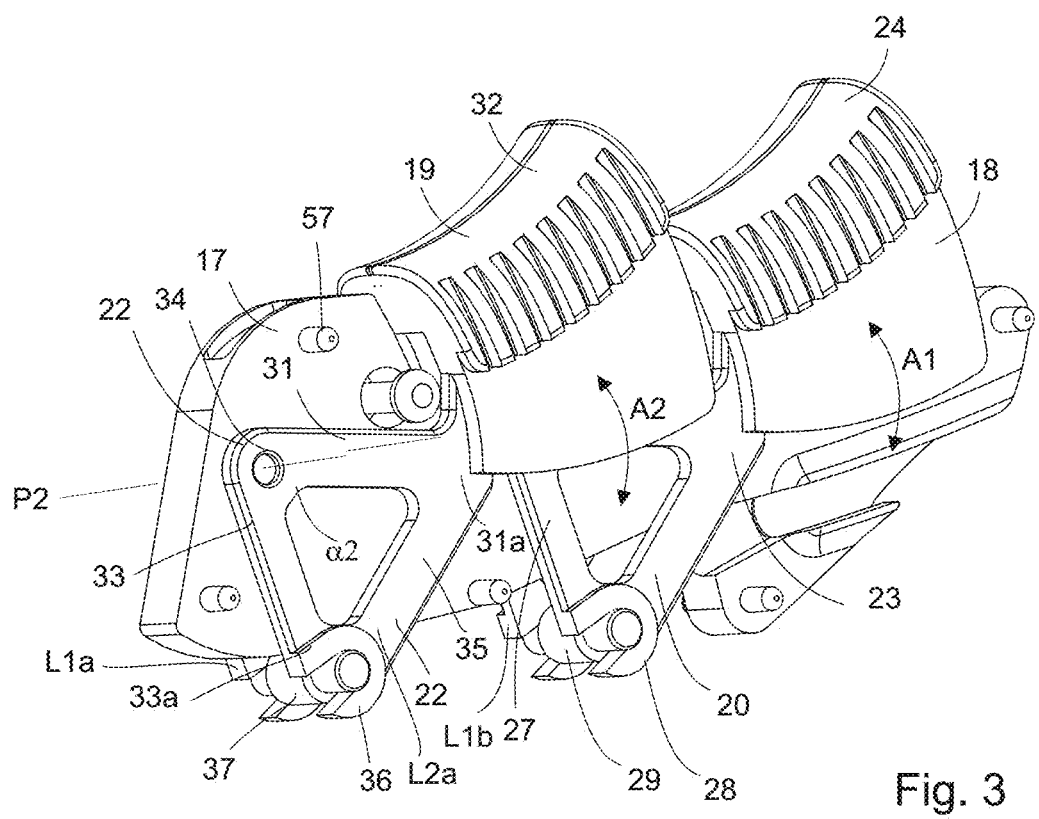
FIG. 3 shows, in an enlarged scale, in perspective from the handle part towards the stylet part of the first embodiment of an endotracheal tube-inserting device, the first string-operating member and the second string-operating member pivotably suspended on the suspension body.
Figure 4:
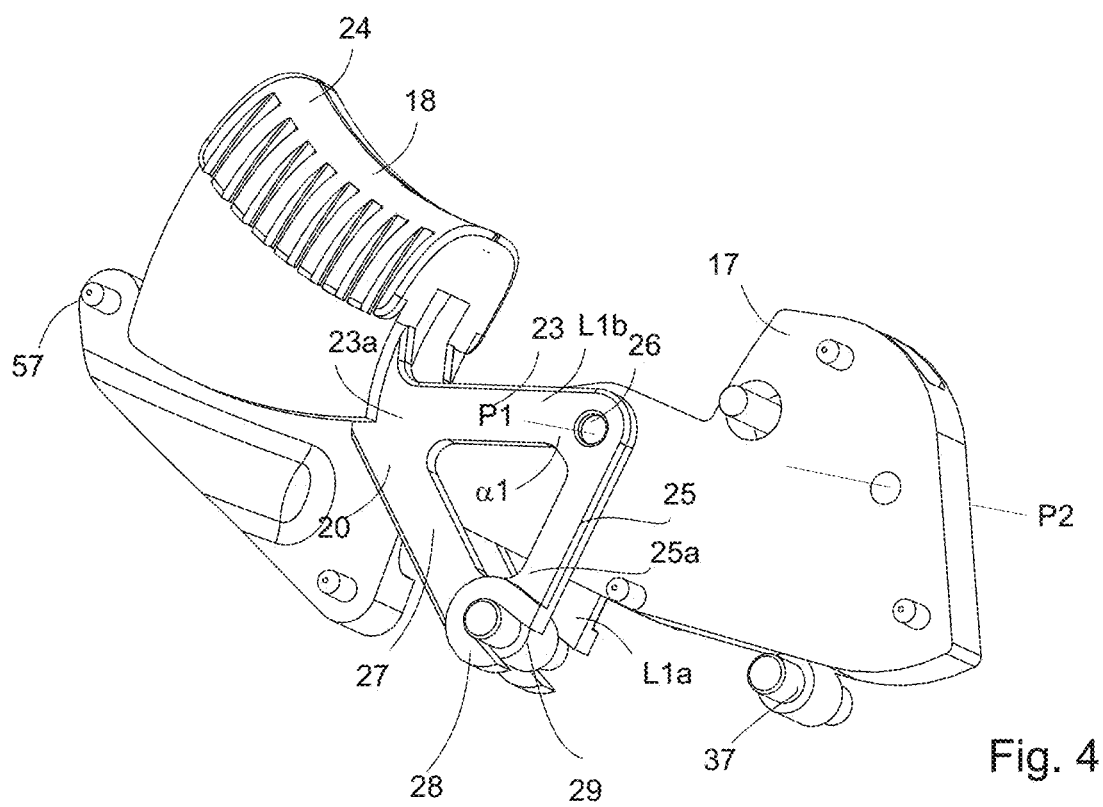
FIG. 4 shows the same without the second string-operating member.

The actuator means 15 of the first embodiment of an endotracheal device 1 includes a suspension body 17, a first string-operating member 18, and a second string-operating member 19 pivotable suspended on the suspension body 17, as seen in more detail in the enlarged views of FIG. 3 and FIG. 4, in which FIGS. 3 and 4 other structural components of the endotracheal tube-inserting device 1 have been left out to better visualize the pivoting "saddle"-arrangement of the string-operating members 18,19 on the suspension body 17.

As seen in FIGS. 3-6 a first string-operating member 18 of the actuator means 15 includes a first bifurcated lever body 20 having opposite first legs L1a, L1b arranged on opposite sides of the suspension body 17 about a first pivot axis P1 to allow the first lever body 20 to move up and down in relation to the suspension body 17, as indicated by double-pointed arrow A1. A second string-operating member 19 of the actuator means 15 includes a second bifurcated lever body 22 having opposite second legs L2a, L2b pivotably arranged about a second pivot axis P2 to allow the second lever body 22 to move up and down in relation to the suspension body 17, as indicated by double-pointed arrow A2.

The opposite first legs L1a, L1b have similar structures, which structures therefore are described in common with reference to a first leg L1b, as seen best in FIG. 4.

The first leg L1b of first lever body 20 has a first actuator lever arm 23 extending from the first pivot axis P1 to a first actuator 24. A first string-operating lever arm 25 extends opposite the first actuator lever arm 23 so that a first fulcrum 26 is established at the first pivot axis P1. A first angle α1 between the first actuator lever arm 23 and the first string-operating lever arm 25 are typically equal to or less than 90°, but a first angle α1 larger than 90 is not excluded. The first actuator lever arm 23 and the first string-operating lever arm 25 are connected to each other via a first intermediate arm 27 extending between the end 23a of the first actuator lever arm 23, at the transition of the first actuator lever arm 23 into the first actuator 18, and the end 25a of the first string-operating lever arm 25 opposite the first pivot axis P1 to confer structural strength to the first lever body 20. These three first arms, thus the first actuator lever arm 23, the first string-operating lever arm 25, and the first intermediate arm 27 together form an open triangular shape that makes the first lever body 20 lightweight and simple to mold, e.g. of a polymeric plastic material, such as a thermosetting material, without losing the structural and dimensional strength needed for reliable and safe operation of the actuator means 15. The end 25a of the first string-operating lever arm 25 opposite the first pivot axis P1 has a first cavity or a first hook 28 for engaging a first string-securing member 29, to which a first proximal string end 30a of the first string member 10 is connected, so that actuating the first string-operating member 18 by applying a force to the first actuator 24 makes the first lever body 20 pivot about the first pivot axis P1 thereby moving the engaging first string-securing member 29 and first hook 28, or similar mating grasping means, lengthwise backwards inside the housing 9 to tension the first string member 10, which has a first distal string end 30b secured to the tip-shaping member 5, and pull the first string-securing location (not shown) at the tip-shaping member 5 away from the distal stylet end 7, thereby bending the tip-shaping member 5, and thus the tubular cover 12, that keeps movement of the first string member 10 and the tip-shaping member 5 under control, and prevents unintended lateral movement of any of the tip-shaping member 5 and the first string member 10 beyond the border of the tubular cover 12.

The opposite second legs L2a, L2b of the second lever body 22 have similar structure, which structure therefore is described in common with reference to a second leg L2a.

The second lever body 22 has a structure similar to the structure of the first lever body 20 and works in a similar manner. Accordingly, a second leg L2a of the second lever body 22 has a second actuator lever arm 31 extending from the second pivot axis P2 to a second actuator 32. A second string-operating lever arm 33 extends opposite the second actuator lever arm 31 so that a second fulcrum 34 is established at the second pivot axis P2. A second angle α2 between the second actuator lever arm 31 and the second string-operating lever arm 33 is outlined similarly to the first angle α1. The second actuator lever arm 31 and the second string-operating lever arm 33 are connected to each other via a second intermediate arm 35 extending between the end 31a of the second actuator lever arm 31, at the transition of the second actuator lever arm 31 into the second actuator 32, and the free end 33a of the second string-operating lever arm 33 opposite the second pivot axis P2, to confer structural strength to the second lever body 22. As for the first lever body 20 these three second arms, thus the second actuator lever arm 31, the second string-operating lever arm 33, and the second intermediate arm 34 together forms an open triangular shape. The end 33a of the second string-operating lever arm 33 opposite the second pivot axis P2 has a second cavity or a second hook 36 for engaging a second string-securing member 37, to which a second proximal string end 38a of the second string member 11 is connected. Actuating the second string-operating member 22 by applying a force to the second actuator 32 makes the second lever body 22 pivot about the second pivot axis P2 thereby moving the engaging second string-securing member 37 and second hook 36, or similar mating grasping means, simultaneously, lengthwise backwards inside the housing 9 to tension the second string member 11, which has a second distal string end 38b secured to the tip-shaping member 5, and pull the second string-securing location (not shown) at the tip-shaping member 5 away from the distal stylet end 7, thereby bending the tip-shaping member 5 by tensioning the second string-securing location. The second string-operating member 19 pulls at another string-securing location than the first string-securing location. In this manner it becomes possible to bend the bendable tip part 5 almost arbitrary and smoothly into any level of S-shape, mirror S-shape, C-shape or J-shape depending on the level of force applied to the respective actuators 24;32.

The bendable tip part 5 can thus be given a variety of bended shapes, and bending be customized for a certain airway anatomy by tensioning and relaxing tensioning of the respective string members 10,11 by operating the associated actuators, which considerably improves the ability of unobstructed passing of the stylet part 3 in between the vocal cords, even for difficult airways.

The first string-operating member 18 and the second string-operating member 19 have similar design and are disposed in spaced relationship along the length of the suspension body 17 to pivot individually at the same time or at different times without jamming.

Figure 5:
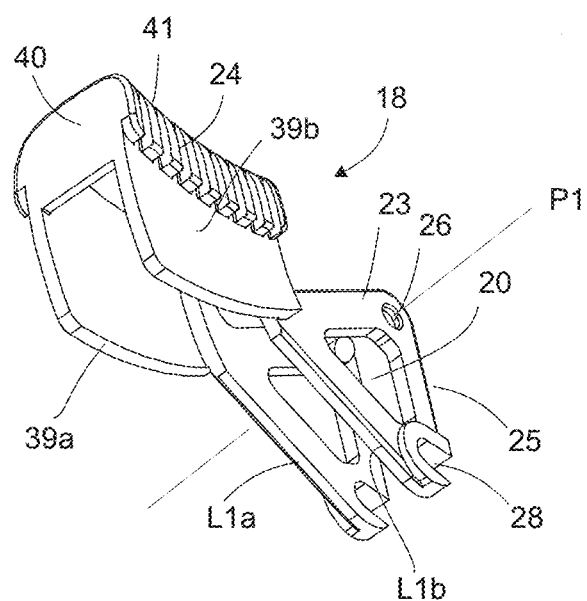
FIG. 5 is a perspective view of a first string-operating member for the first embodiment of an endotracheal tube-inserting device, and seen from below.

As seen best in FIG. 5 the opposite first legs L1a, L1b of the first bifurcated lever body 20 extends into a U-shaped first actuator 24. The opposite first leg L1a, L1b extends into the first actuator legs 39a,39b of the U-shaped first actuator 24, which first actuator legs 39a,39b are connected by first bridging member 40 that has exterior ridges 41 for improved tactileness and increased friction when grasping the handle part 2 for operating and maneuvering the endotracheal tube-inserting device 1.

Figure 6:
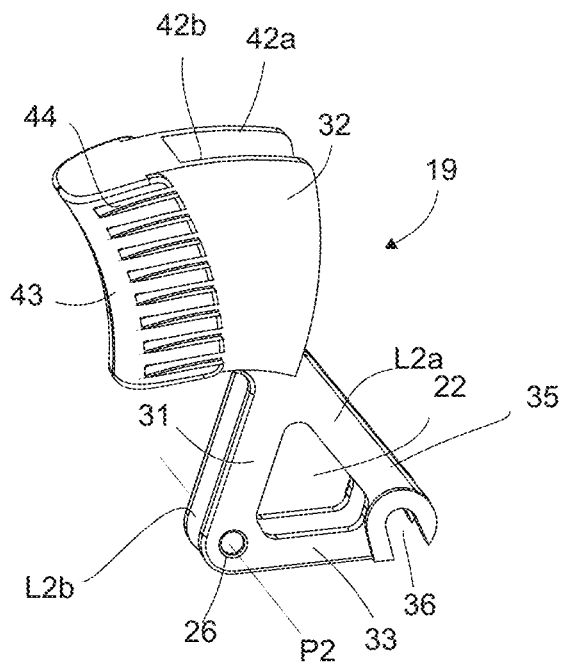
FIG. 6 is a side view of an associated second string-operating member.

The side view of FIG. 6 shows the second string-operating member 19 but since the first string-operating member 18 and the second string-operating member 19 in the present embodiment are identical, FIG. 6 could quite as well show the first string-operating member 18. The opposite second legs L2a, L2b of the second bifurcated lever body 22 extends into a U-shaped second actuator 32. The opposite second leg L2a, L2b extends into the second actuator legs 42a,42b of the U-shaped second actuator 32, which second actuator legs 42a,42b are connected by second bridging member 43 that has exterior ridges 44 for improved tactileness and increased friction when grasping the handle part 2 for operating and maneuvering the endotracheal tube-inserting device 1.

An exemplary string-securing member 29;37 can e.g. be a freely suspended pin extending crosswise between the first shell part 13 and the second shell part 14 inside the housing 9. The pin is not connected to any of the shell parts 13,14 because it shall be able to move in response to pivoting the lever bodies 20,22. The engagement between the hook 28;36 and the string-securing member 29;37 however keeps the string member 10;11 under tension so that the string-securing member 29;37 not accidentally can disengage the hook 28:36 or cavity.

Alternative ways of securing a string member to a lever body in a manner that allows the lever body to pull the string member backward when tensioned and move forward when tension is relieved is within the scope of the present invention. A string member can in the alternative simply be secured by a knot in an eye of the lever body.

Figure 7:
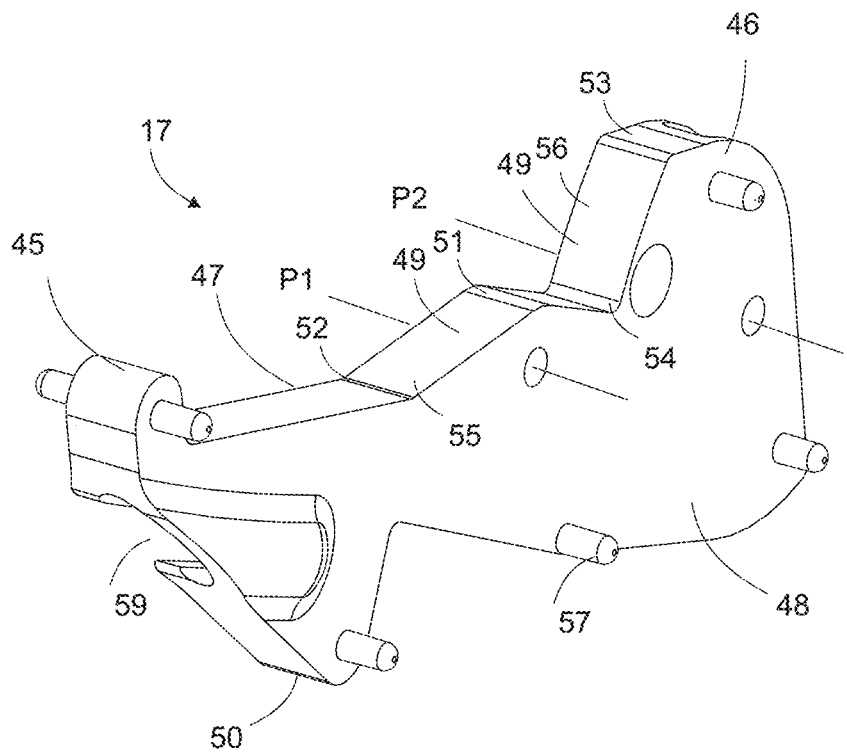
FIG. 7 is an enlarged perspective view of an associated suspension body seen from the proximal end.
Figure 8:
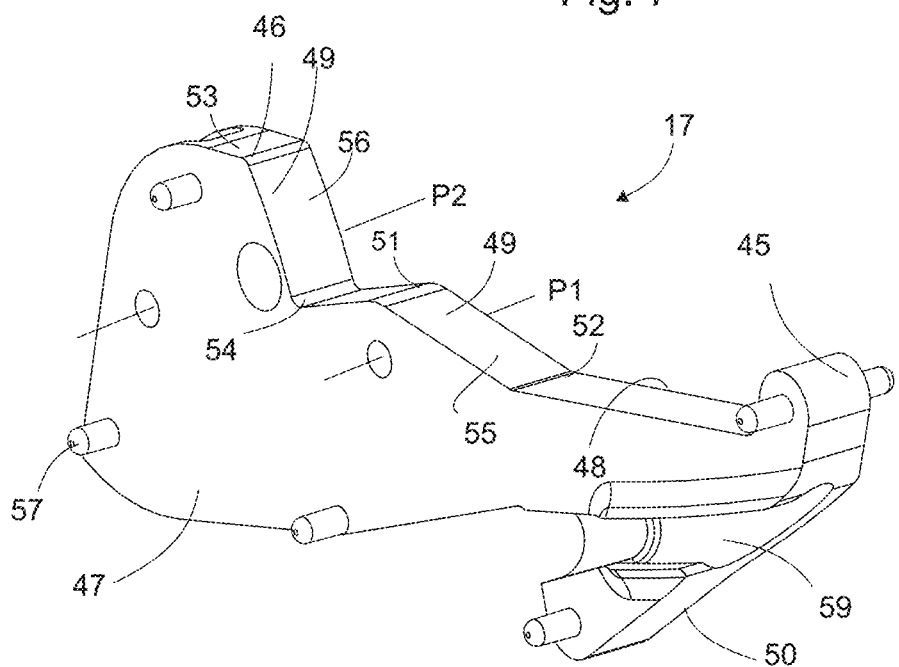
FIG. 8 shows the same seen from the opposite side.

FIGS. 7 and 8 are perspective views of the suspension body 17 that has a distal suspension body end 45 and an opposite proximal suspension body end 46, respectively. The suspension body 17 has opposite lengthwise extending first 47 and second side faces 48, an upper ridge 49 and a lower edge 50 extending lengthwise between said side faces 47,48. The upper ridge 49 is configured with alternating first crest 51 and first sag 52 at the distal suspension body end 45, and second crest 53 and second sag 54 at the proximal suspension body end 46. The alternating arrangement of crests 51,53 and sags 52,54 provides points of discontinuity along the curvature of the upper ridge 49 to define a first seat 55 for the first actuator 24 and a second seat 56 for the second actuator 32 when pivoted about respective pivot axis P1, P2.

Both the opposite first side face 47 and second side face 48 has a plurality of protruding securing pins 57 arranged to mate into corresponding female securing means 58 of the shell parts 13,14 of the housing 9 to secure the suspension body 17 in a manner inside the housing 9 wherein none of the suspension body 17, the securing pins 57 or the female securing means 58, e.g. bush mountings, can obstruct the operation of the actuator means 15 and the tube ejecting mechanism. For the present embodiments of an endotracheal tube-inserting device 1 the securing pins 57 are arranged along or in the vicinity of the annular outer edge of the suspension body 17.

At the distal suspension body end 45 a groove 59 or recess in the first face 48 serves to receive, mount and align the proximal stylet end part 8a of the elongate guide member 4 for securing the elongate guide member 4 firmly to the suspension body 17. Securing can e.g. be achieved by gluing or by traverse pins.

In an alternative embodiment the protruding securing pins 57 can be provided at the shell parts 13,14 and the female securing means 58 be provided at the suspension body 17.

FIGS. 9, 10 and 11 show the shell parts 13,14 apart from each other and in assembled state to obtain the housing 9.

The proximal housing end 61 is closed, whereas the distal housing end 60 is open for passage of at least a length of the proximal stylet end part 8a of the stylet part 3. The upper lengthwise housing edge 62 has a proximal opening 63 for the pivotable passage of the first actuator 24 of the first string-operating member 18 and a distal opening 64 for the pivotable passage of the second actuator 32 of the second string-operating member 19. The first actuator 24 and the second actuator 32 constitute the buttons, which the operator uses to confer a desired curvature and shape to the distal tip part 6.

As seen in e.g. FIGS. 1 and 2 a tube ejecting mechanism 65 to get the endotracheal tube (not shown) off the stylet part 3 includes a ratchet mechanism 66 with a third actuator 67 that protrudes from the housing 9 opposite the proximal opening 63 and the distal opening 64.

Figure 13:
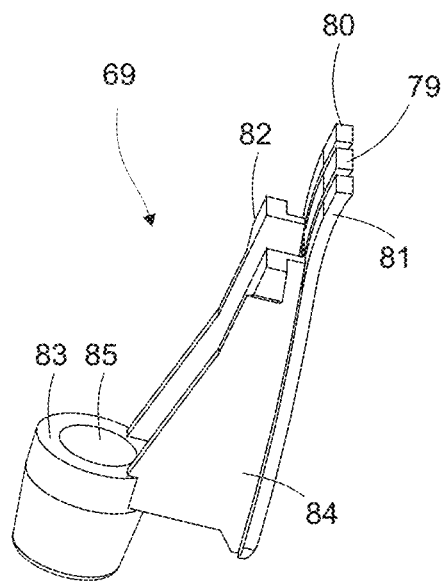
FIG. 13 is a perspective view seen from the tube connector of a wedge part of a tube ejecting mechanism for use with the third rack part.

The ratchet mechanism 66 has a rack part 68 and a wedge part 69, which wedge part 69 is seen in FIG. 13.

The rack part 68 is has an elongate first stationary rack part 70, an elongate second stationary rack part 71 and an elongate moveable third rack part 72, which elongate moveable third elongate rack part 72 is shown in FIG. 12.

The elongate moveable third rack part 72 is, as shown in FIG. 2, disposed between the elongate first stationary rack part 70 and the elongate second stationary rack part 71. The three rack parts 70,71,72 extend lengthwise from the proximal housing end 61 towards the distal housing end 60 inside the housing 9 opposite the proximal opening 63 and the distal opening 64.

The third actuator 67 of the elongate moveable third rack part 72 protrudes through an ejector slot 74 in the housing 9 towards the proximal housing end 61 opposite the proximal opening 63 and the distal opening 6 for pivotable passage of the actuators 24,32. Thus the third actuator 67 is provided at a proximal end 73 of the elongate moveable third rack part 72 to be accessible to move said elongate moveable third rack part 72 in a translatory movement that is restricted by the ejector slot 74 towards the bendable tip part 6.

The elongate moveable third rack part 72, which is shown in the separate view of FIG. 12, is suspended inside the housing 9 by means of a spring 75 or similar resilient means, such as an elastic strap. The spring 75 is stretched and tensioned when the elongate moveable third rack part 72 is moved lengthwise along the housing 9 upon a stroke of the third actuator 67 in order to displace the elongate moveable third rack part 72 forward between the elongate first stationary rack part 70 and elongate second stationary rack part 71.

The elongate first stationary rack part 70 has first teeth 76, the elongate second stationary rack part 71 has second teeth 77, and the elongate moveable third rack part 72 has third teeth 78.

Figure 15:
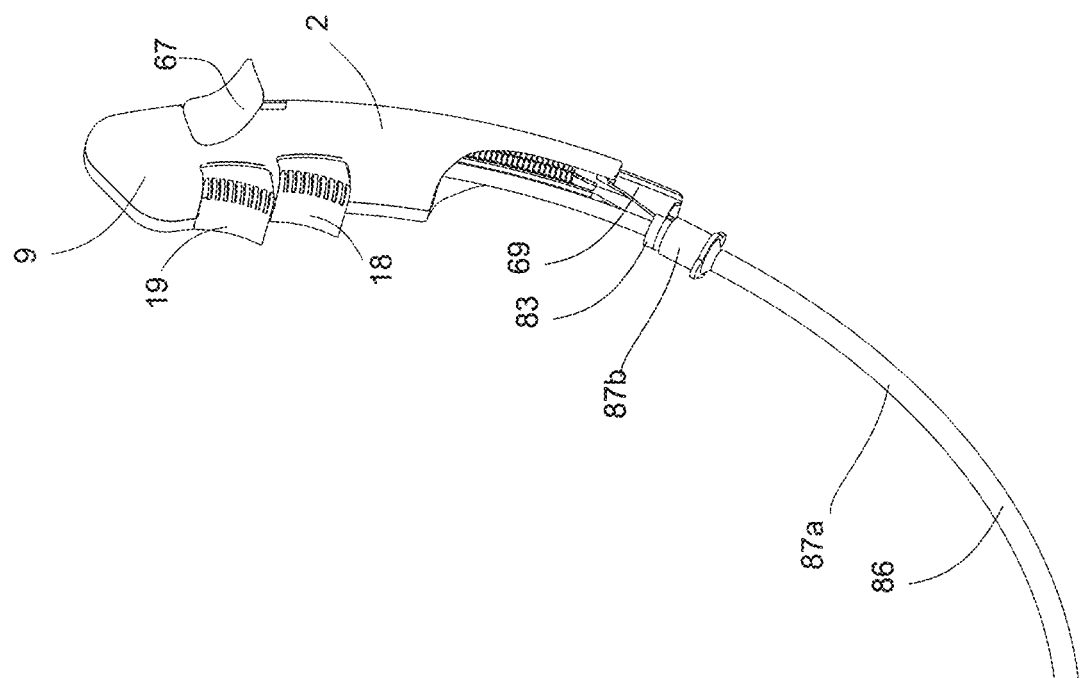
FIG. 15 is a perspective general side view of the first embodiment of an endotracheal tube-inserting device in an ejecting step of the endotracheal tube.
Figure 14:
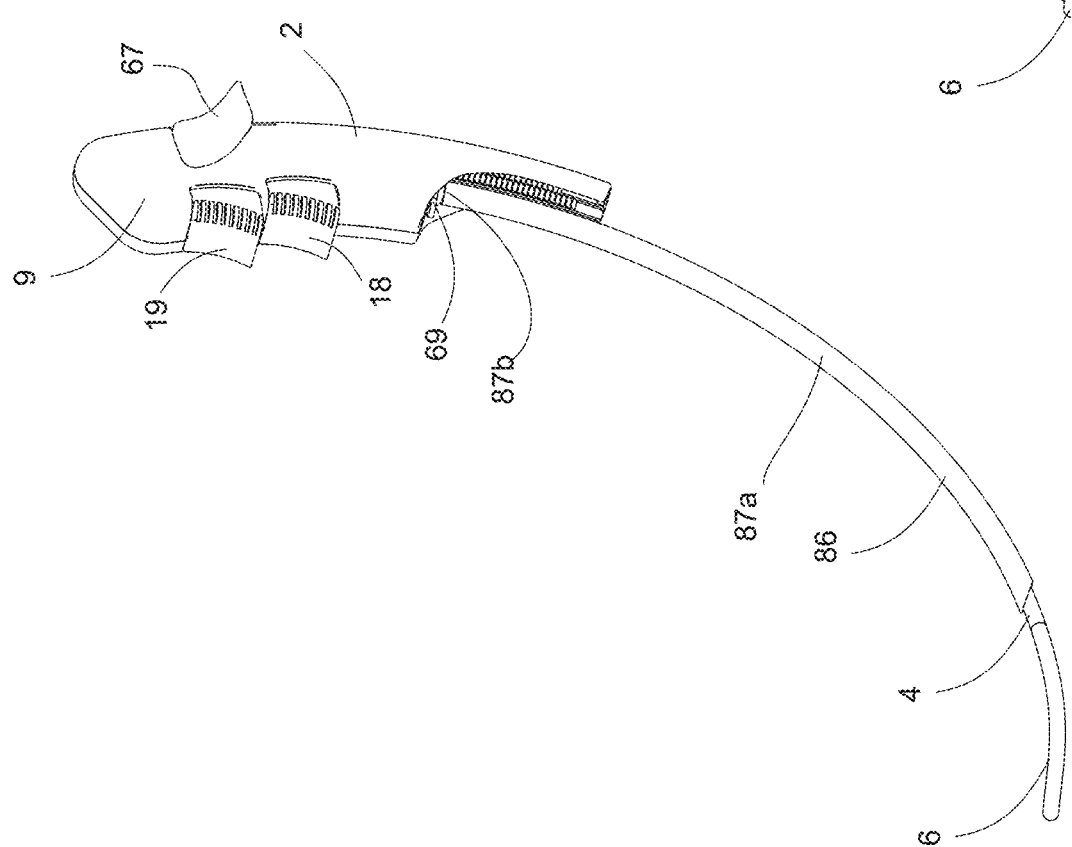
FIG. 14 is a perspective general side view of the first embodiment of an endotracheal tube-inserting device having an endotracheal tube sheathed on the stylet part prior to use.

As shown in the perspective view of FIG. 13, and in FIGS. 16-19 the wedge part 69 has a center wedge part 79 that engages between the third teeth 78 of the elongate moveable third rack part 72. The center wedge part 79 is located between a first lateral wedge part 80 to engage the first teeth 76 of the elongate first stationary rack part 7 and a second lateral wedge part 81 to engage the second teeth 77 of the elongate second stationary rack part 71. The center wedge part 79, the first lateral wedge part 80, and the second lateral wedge part 81 are provided at a proximal end 82 of the wedge part 69 and a tube connector 83 is provided at the distal wedge part 84. The tube connector 83 is a cylindrical tapering plug with a bore 85 for receiving the elongate guide member 4 to allow the wedge part 69 to be fitted in fixed position on said elongate guide member 4, or preferably to slide along said elongate guide member 4 in response to operating the third actuator 67 and thus the movable third elongate rack 72 to eject an endotracheal tube 86, as shown in general in FIGS. 14 and 15.

The endotracheal tube 86 has a tube part 87a and an airway connector 87b that mates around the tube connector 83 of the wedge part 69, to push the endotracheal tube 86 off the elongate guide member 4 when the third actuator 67 of the elongate moveable third rack part 72 displaces the wedge part 69 and thus the endotracheal tube 86 forward towards the distal stylet end 7.

The ejecting steps are seen more clearly in FIGS. 16-19. The state shown in FIGS. 16 and 17 corresponds to the state shown in FIG. 14, and the state shown in FIGS. 18 and 19 corresponds to the state shown in FIG. 15 where the endotracheal tube 86 has been moved closer to the distal tip part 6 by means of the tube ejecting mechanism 65.

Figure 17:
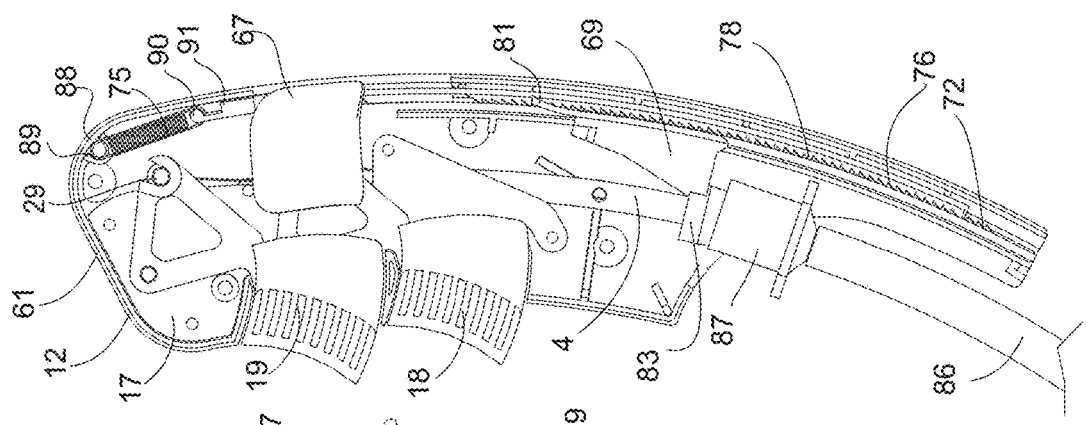
FIG. 17 shows the same seen from the side.
Figure 16:
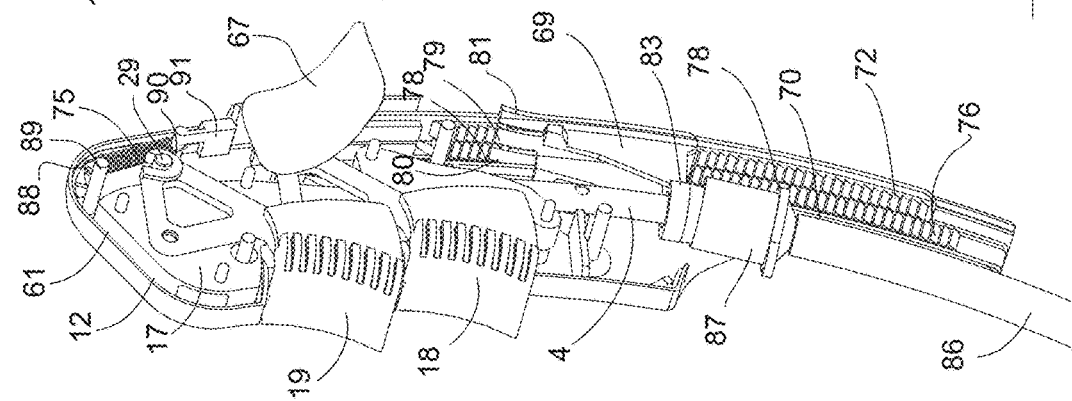
FIG. 16 is an enlarged scale, perspective, fragmentary view of the handle part of the first embodiment of an endotracheal tube-inserting device, without the second shell part, and where the proximal end of the stylet part is provided with an endotracheal tube positioned in the starting position prior to the endotracheal procedure.

In FIGS. 16 and 17 the second shell part 14 has been removed to illustrate the interior components and structures more or less accommodated by the handle part 2. The positions of the wedge part 69 in relation to the elongate stationary rack parts 70, 71, the third actuator 67, and the elongate moveable third rack part 72 of the ratchet mechanism 66 inside the housing 9 is shown in the starting position ready for the endotracheal procedure. The elongate moveable third rack part 72 is in retracted position in the housing 9, and the spring 75, that has one spring end 88 secured at a spring securing location 89 inside the proximal housing end 61 of the housing 9, and an opposite end 90 secured to the proximal end 91 of the elongate moveable third rack part 72, is in relaxed state. An endotracheal tube 86 is sheathed on the elongate guide member 4, and the airway connector 87 of the endotracheal tube 86 mates around the tube connector 83 of the wedge part 69.

Figure 19:
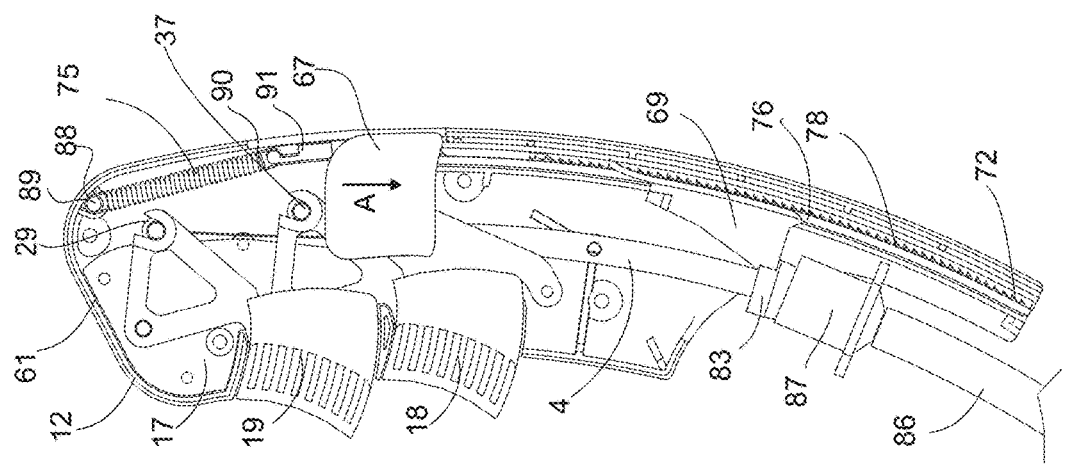
FIG. 19 shows the same seen from the side.
Figure 18:
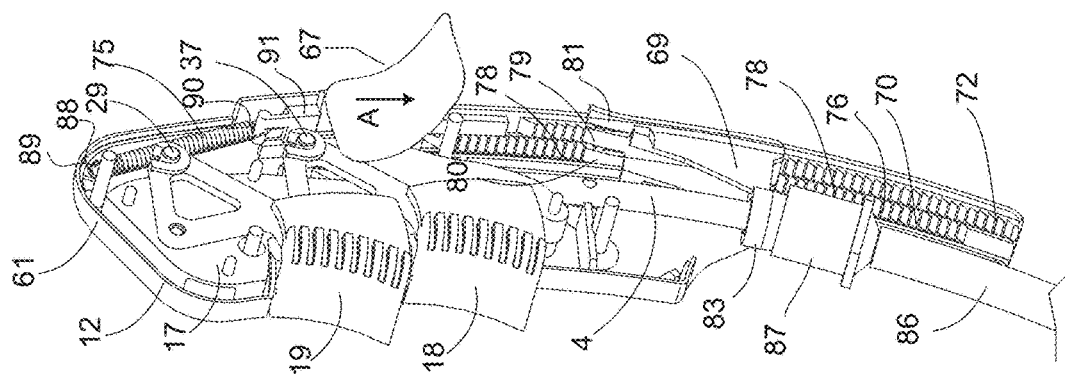
FIG. 18 shows the same as FIG. 15 but in an ejecting state.

When the third actuator 73 is depressed in the direction of the bendable tip part 6 by application of a force, as indicated by arrow A in FIGS. 18 and 19, the engaging center wedge part 79 and third teeth 78 of the elongate moveable third rack part 72 travel along. During a stroke of the third actuator 67 the engaging tube connector 83 and airway connector 87 of the endotracheal tube 86, and thus also said endotracheal tube 86, are moved a stroke length closer to the bendable tip part 6. At the end of the travel of the stroke, the first 80 and second lateral wedge parts 81 engage the adjacent first teeth 76 and the second teeth 77 so that the wedge part 69 cannot return towards the proximal housing end 61 when the elongate moveable third rack part 72 returns to the proximal housing end 61 to repeat the stroke. When the elongate moveable third rack part 72 has returned to the relaxed condition of the spring 75, another third tooth or section of third teeth 78 closer to the distal end 92 of the elongate moveable third rack part 72 is made available and exposed for further displacing the wedge part 69 yet a stroke forward by its engagement with the center wedge part 79. Strokes can be repeated as long as the length of the elongate moveable third rack part 72 is available for engagement with the center wedge part 79. When the wedge part 69 reaches or is close to the distal end 92 of the elongate moveable third rack part 72 further strokes cannot move the wedge part 69 further forward. The tube connector 83 may not automatically or immediately be released from the airway connector 87 to leave the endotracheal tube 86 in trachea for subsequent connection to an appropriate ventilation equipment upon retraction of the stylet part 3. Instead the operator may choose to set the endotracheal tube 86 free before the wedge part 69 reaches the distal end 92 of the elongate moveable third rack part 72. Accordingly, the operator may choose to separate the endotracheal tube 86 and the endotracheal tube-inserting device 1 at any convenient stage during the endotracheal procedure.

Figure 20:
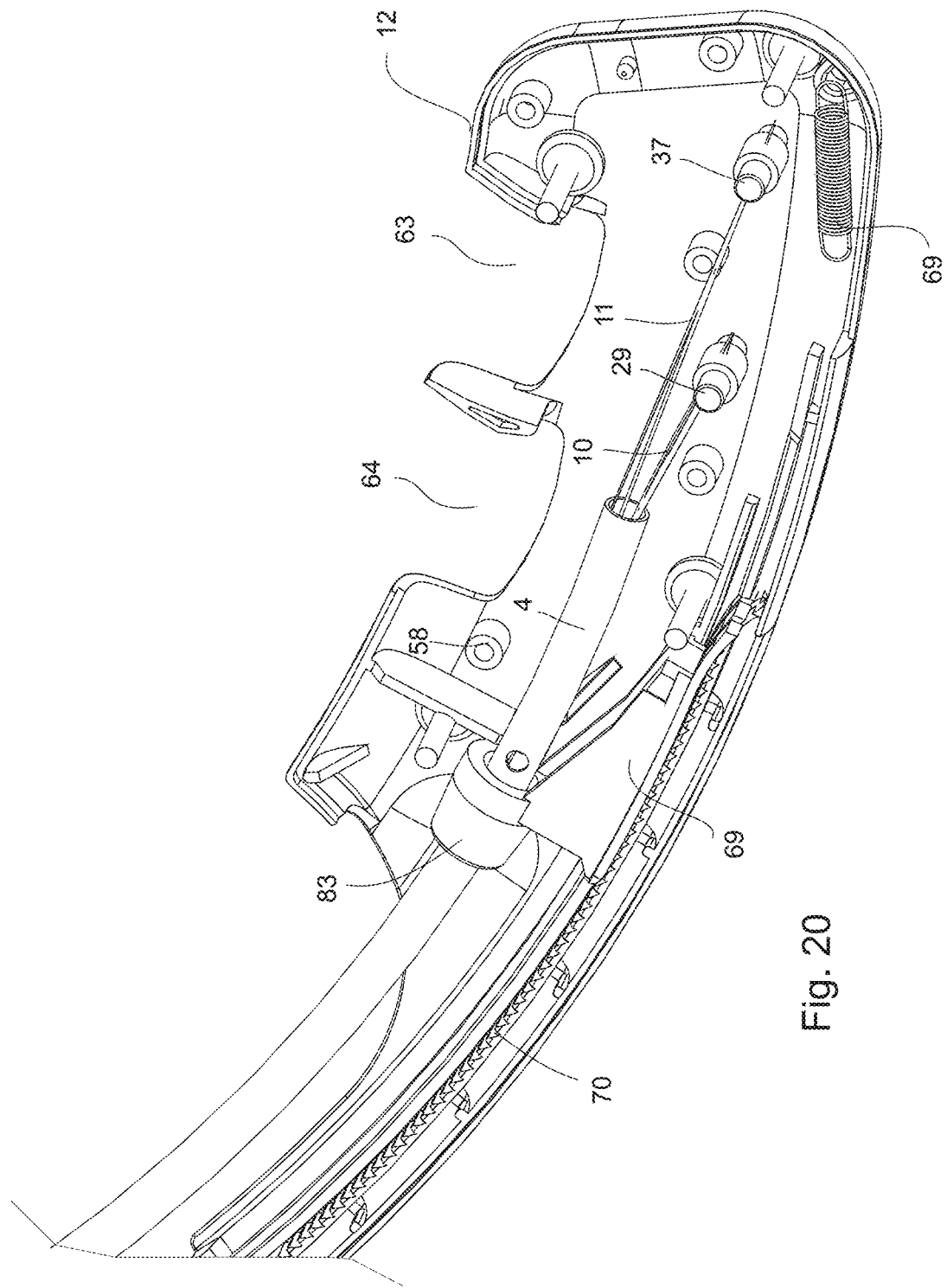
FIG. 20 is a view inside the first shell part of the first embodiment of an endotracheal tube-inserting device, seen from the side, with the wedge part and the strings securing members exposed via the elongate guide member, however without endotracheal tube, and wherein the suspension body, the third moveable rack part and the string-operating members also have been left out.

As seen in FIG. 20 the first string member 10, e.g. a metal wire, is secured to the first string-securing member 29, e.g. a cross pin, freely floating in the housing or being supported again the shell walls. Similarly, the second string member 10, e.g. a metal wire, is secured to the second string-securing member 37, e.g. a cross pin, lengthwise offset the first string member 10. The string-securing members 29;37 are grasped by the first string-operating member 18, and the second string-operating member 19, respectively, as described above, to pull the string members 10,11, simultaneously or independently, to same or different extent, in and out of the elongate hollow member 4 a distance corresponding to up to the maximum length achievable by a full depression and pivoting of a string-operating member.

This novel and inventive configuration and design of an endotracheal tube-inserting device 1 provides a multitude of options and a huge degree of freedom for configuring the shape of the bendable tip part 6 to adopt a shape suited for maneuvering in almost any imaginable airway anatomy.

Various examples of curvatures and shapes that can be given to the bendable tip part 6 by operating the tip part operating member 16 using the actuator means 15 is shown in the subsequent FIGS. 21-24. The endotracheal tube-inserting device 1 shown in FIGS. 21-24 is shown with transparent elongate guide member 4 and transparent tubular cover 12 to illustrate that the first string member 10 and the second string member 11 extend along the length of said elongate guide member 4 and further inside the tubular cover 12, inside which the tip-shaping member 5 is located. The first string member 10 is secured at a first string-securing location 93 retracted from the first end 95 of the tip-shaping member 5, in the present case on top of a tip-shaping member 5 in form of a plate spring, to be operated by means of the first actuator 24, as indicated by curved arrow A1. The second string member 11 is secured to the tip-shaping member 5 at the bottom of the tip-shaping member 5 at a second string-securing location 94 downstream the first string-securing location 93 to be operated by means of the second actuator 32, as indicated by curved arrow A2. Thus the first string-securing location 93 is both lateral and lengthwise offset the second string-securing location 94 and closer to the handle part 2, as seen more clearly in the associated FIG. 24, which is an enlarged scale view of the bendable tip part 6 seen in FIG. 23.

Figure 21:
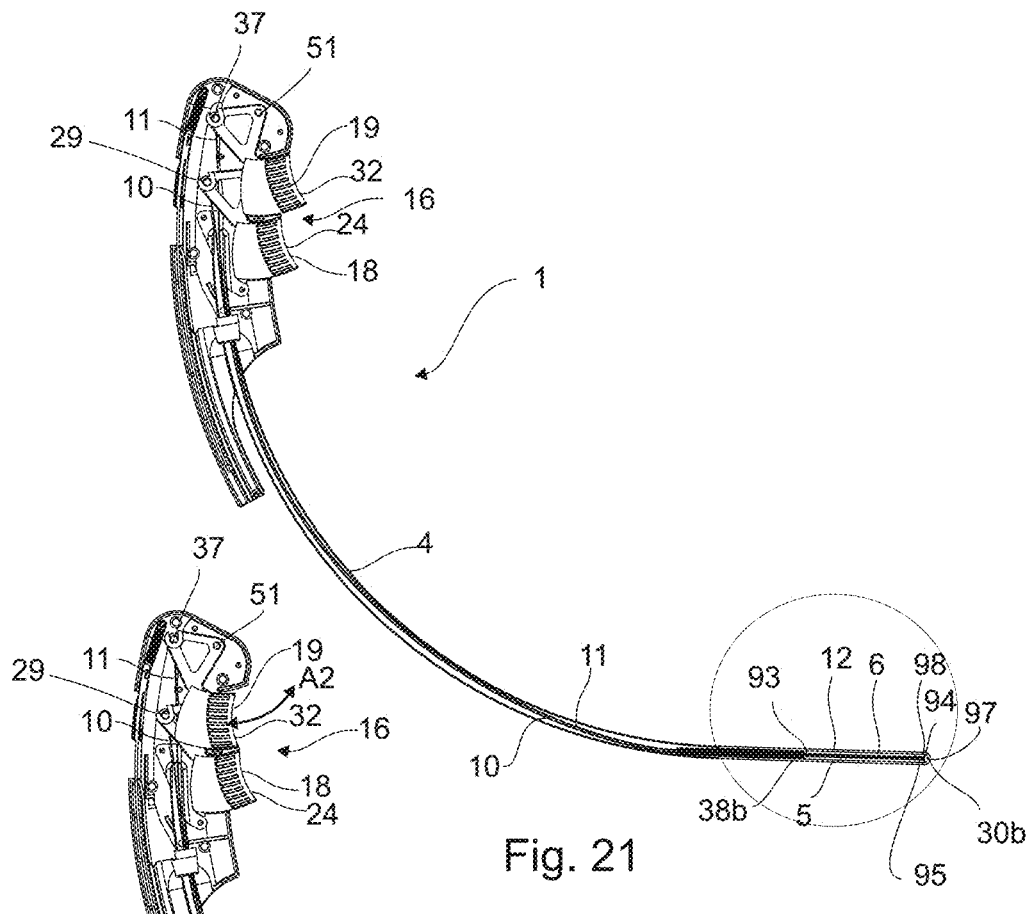
FIGS. 21-24 show bending steps and configurations of a first embodiment of a bendable tip part having both lateral and lengthwise offset first and second securing locations.

In FIG. 21 neither the first string-operating member 18 nor the second string-operating member 19 are pivoted and the bendable tip part 6 are straight without any bending(s). Neither the first string-securing location 93 nor the second string-securing location 94 have been activated.

Figure 22:
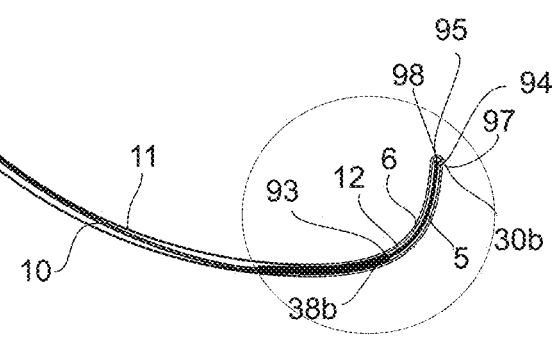

In the situation shown in FIG. 22 only the second string-operating member 19 has been actuated by depressing the second actuator 32, as indicated by arrow A2. Pressing on the second actuator 32 moves the second string-securing member 37 back inside the housing 9 whereby the second string-securing location 94 is pulled closer to the handle part 2, to provide the bendable tip part 6 with a C-shape wherein the free distal tip 97 of the bendable tip part 6 has been turned upwards, referring to the orientation seen FIG. 22.

Figures 23, 24:
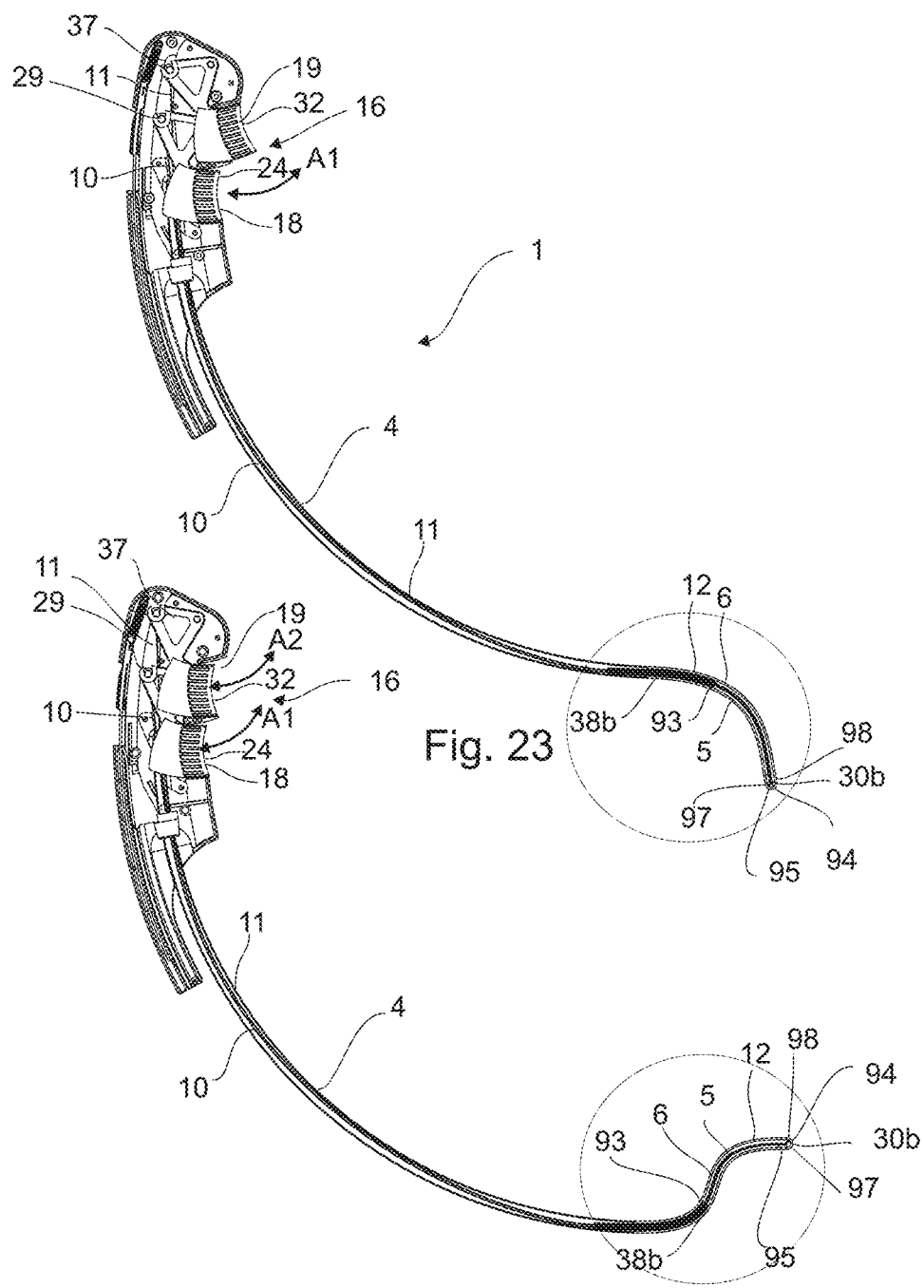

In the situation shown in FIG. 23 only the first string-operating member 18 has been actuated by depressing the first actuator 24, as indicated by arrow A1. Pressing on the first actuator 24 moves the first string-securing member 29 back inside the housing 9 whereby the first string-securing location 93 is pulled closer to the handle part 2, to provide the bendable tip part 6 with a J-shape, wherein the distal free distal tip 97 of the bendable tip part 6 has been turned downwards, using the orientation of FIG. 23.

In the situation shown in FIG. 24 both the first string-operating member 18 and the second string-operating member 19 have been actuated by depressing the first actuator 24, as indicated by arrow A1, and the second actuator 32, as indicated by arrow A2. Pressing on both the actuators 24,32 move both string-securing members 29,37 back inside the housing 9 whereby both string-securing locations 93,94 are pulled closer to the handle part 2, to provide the bendable tip part 6 with an S-shape.

Because the tip-shaping member 5 is confined inside the tubular cover 12, any possible movement by the tip-shaping member 5 in response to operation of the actuators 24,32 are also controlled and confined by the presence of said tubular cover 12 that restricts lateral movement of the plate spring 5a beyond the border of the tubular cover 12, but permits at least lengthwise bending because of flexibility of the tubular cover 12 of the bendable tip part 6.

Various levels of force applied to the actuators 24,32 facilitate the provision of even further shapes than the shapes shown in FIGS. 21-24.

Figure 25:
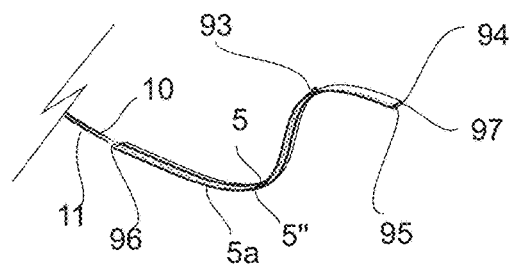
FIG. 25 is an enlarged scale view of the tip-shaping member in the S-configuration seen in FIG. 23.

FIG. 25 is an enlarged scale view of the first embodiment of a tip-shaping member 5 in the S-configuration seen in FIG. 24.

Figure 27:
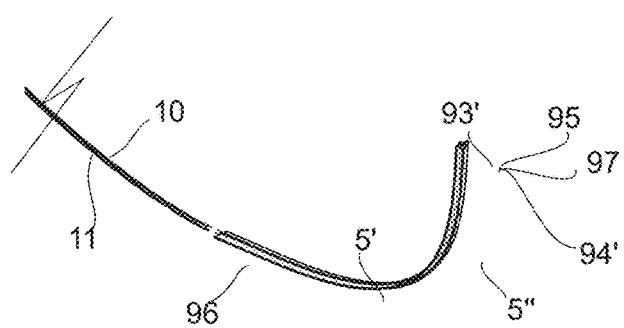
FIG. 27 is an enlarged scale view of a modified bendable tip part bend into C-shape.
Figure 28:
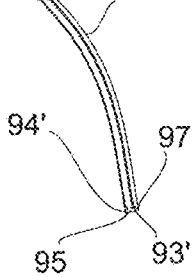
FIG. 28 is an enlarged scale view of the same bend into a J-shape.
Figure 26:
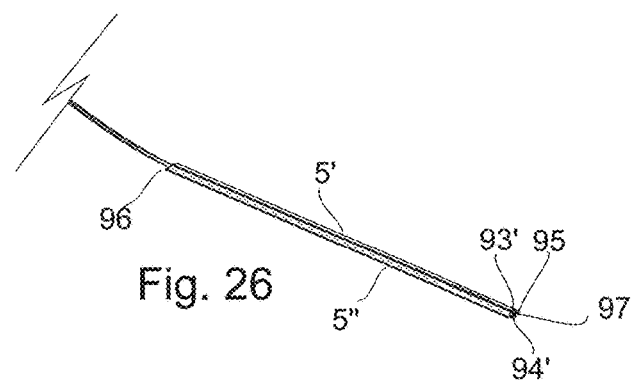
FIG. 26 is an enlarged scale view of a modified bendable tip part in straight configuration.

A second embodiment of a tip-shaping member 5' is seen in FIGS. 26, 27 and 28. The shapes and configuration of the bendable tip part 6 shown in FIGS. 21, 22 and 23 can also be obtained by implementation of the second embodiment of a tip-shaping member 5', which second embodiment of a tip-shaping member 5' has laterally offset first string-securing location 93' and second string-securing location 94'. Thus for the second embodiment of a tip-shaping member 5' the string-securing locations 93', 94' are not lengthwise offset. Using the orientation shown in FIGS. 26, 27, and 28 the first string-securing location 93' is on top side of the tip-shaping member 5', e.g. a plate spring member 5", and the second string-securing location 94' is on the bottom side of the tip-shaping member 5', using the orientation seen in FIGS. 26, 27 and 28.

In FIG. 26 the second embodiment of a tip-shaping member 5' is in a relaxed condition corresponding to the condition shown in FIG. 21 for the first embodiment of a tip-shaping member 5.

In FIG. 27 the second embodiment of a tip-shaping member 5' is in same C-shaped configuration as in FIG. 22, and in FIG. 28 the second embodiment of a tip-shaping member 5' is in a J-shaped configuration similar to the configuration shown in FIG. 23.

Figure 29:
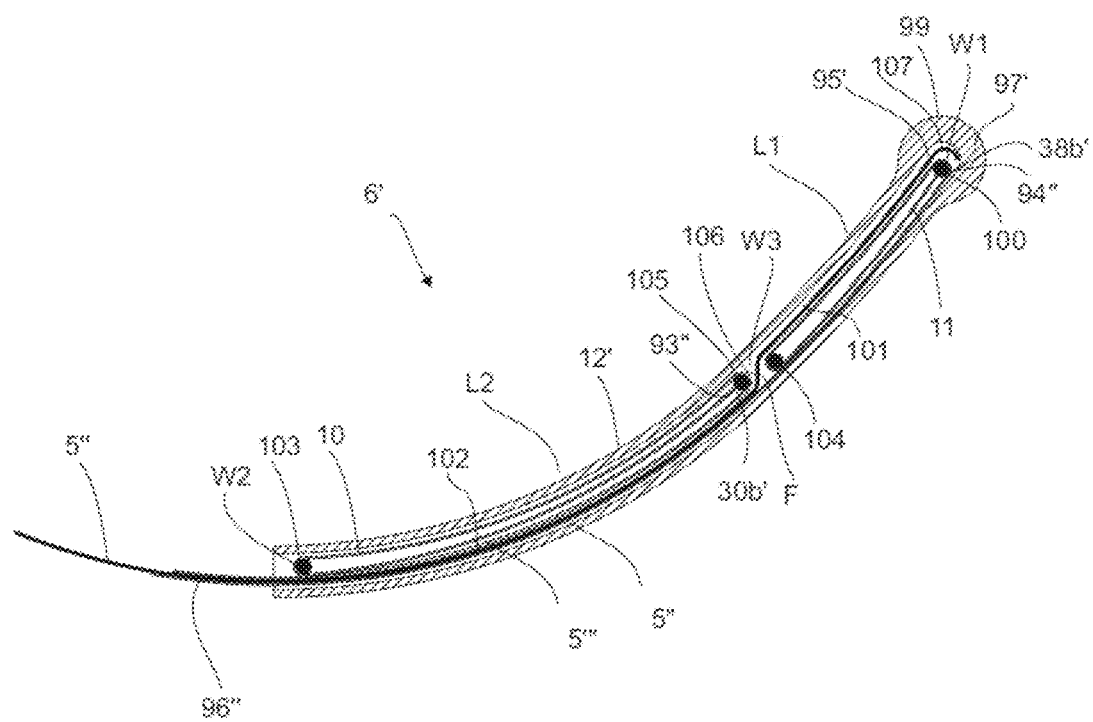
FIG. 29 is a lengthwise sectional view through a third embodiment of a bendable tip part.

FIG. 29 is a lengthwise sectional view through a third embodiment of a bendable tip part 6' having a third embodiment of a tip-shaping member 5"" in form of a flat plate spring member 5" of spring steel with pulley wheels arranged inside a tubular cover 12'. The first end 95" of the tubular cover 12' is configured with a flexible resilient tip 99, the function of which will be described in further details in relation to FIGS. 29-34. The first string-securing location and the second string-securing location are defined substantially as for the first embodiment of a bendable tip part 6 shown in FIG. 25 and for like part same reference numerals are used.

The bendable tip part 6' has a distal pulley wheel 100 provided on a bottom side 101 of the plate spring member 5" at a first pulley wheel location W1 at the free distal tip 97' of the distal tip part 6', a proximal pulley wheel 103 is provided on a top side 102 of the at least one plate spring member 5" opposite the first side 101 at a second pulley wheel location W2 spaced apart from the first pulley wheel location W1, using the orientation shown in FIG. 29. A distal intermediate pulley wheel 104 and a proximal intermediate pulley wheel 105 are provided adjacent each other on opposite sides 101,102 of the plate spring member 5" at an intermediate pulley wheel location W3 between the first pulley wheel location W1 and the second pulley wheel location W2. The plate spring member 5" passes between the distal intermediate pulley wheel 104 and the proximal intermediate pulley wheel 105 so that the distal intermediate pulley wheel 104 is provided on the bottom side 101 of the plate spring member 5" and the proximal intermediate pulley wheel 105 is provided on the top side 102 of the plate spring member 5", and so that the arrangement of the intermediate pulley wheels 104,105 establishes, as indicated by reference numeral F, a fixed pivot point or fixed pivot location.

The first string member 10 is secured at a first string-securing location 93" to the proximal intermediate pulley wheel 105 at the intermediate pulley wheel location W3, e.g. to an axle (not shown) of the proximal intermediate pulley wheel 105 or to the plate spring member 5" at a similar suitable location The second string member 11 is secured at a second string-securing location 94" to the distal pulley wheel 100 at the first pulley wheel location W1, e.g. secured to an axle (not shown) of the distal pulley wheel 100 or to the plate spring member 5" at a similar suitable location.

The plate spring member 5" has a pre-shaped curvature and a Z-bending 106 is present at the fixed pivot location at the intermediate pulley wheel location W3. The Z-bending allows the plate spring member 5" to pass between the intermediate pulley wheels 104,105 when the plate spring member 5" is in its curved configuration and so that the pulley wheels can act on the respective side of plate spring member 5". The Z-shaped bending 106 can be fully straightened, e.g. i needed to insert the bendable tip part into the endotracheal tube that should be guided in place inside trachea.

The Z-shaped bending 106 of the curved bendable tip part 6' can offset the lengths of the plate spring member 5" on opposite sides of the intermediate pulley wheel location W3 to different degree, although the degree of offset between the parallel legs of the Z-shape is restricted by the internal diameter of the tubular cover 12', and by the fact that the string members 10,11 shall be able to be pulled and operated easily by the string-operating members.

The first end 95' of the tip-shaping member 5''' has a C-shaped bending 107 that passes around the distal pulley wheel 100. Such a C-shaped bending 107 is optional.

The first distal string end 30b' of the first string member 10 is secured to the proximal intermediate pulley wheel 105 wherefrom the first string member 10 runs around the proximal pulley wheel 103 back to the proximal intermediate pulley wheel 105 and around said proximal intermediate pulley wheel 105 back beyond the proximal pulley wheel 103 for having a first proximal string end 30a' operatively secured to a corresponding first string-operating member associated with the handle part. The second distal string end 38b' is secured to the distal pulley wheel 100 wherefrom the second string member 11 runs around the distal intermediate pulley wheel 104 back to the distal pulley wheel 100 and around said distal pulley wheel 100 and back beyond the distal intermediate pulley wheel 104 and further on beyond the proximal pulley wheel 103 for having a second proximal string end 38a' operatively secured to a corresponding second string-operating member associated with the handle part.

Different lengths of between 7-15 cm of the bendable tip part have been tested. FIG. 30-33 illustrate various bend configurations of the third embodiment of the bendable tip part 6' seen in FIG. 29.

The proximal length, which faces the patient and which is the portion of the bendable distal tip part 6' between the proximal pulley wheel 103 and the proximal intermediate pulley wheel 105, is indicated by reference numeral L2. The distal length of the bendable distal tip part 6' between the distal intermediate pulley wheel 104 and the distal pulley wheel 100 is indicated by reference numeral L2, which distal length L1 is the portion of the bendable distal tip part 6' in extension of the proximal length and end in the free distal tip 97'.

In the exemplary third embodiment of a bendable tip part 6' shown in FIGS. 30-34 L2>L1 and L1+L2 is 10 cm.

Figure 30:
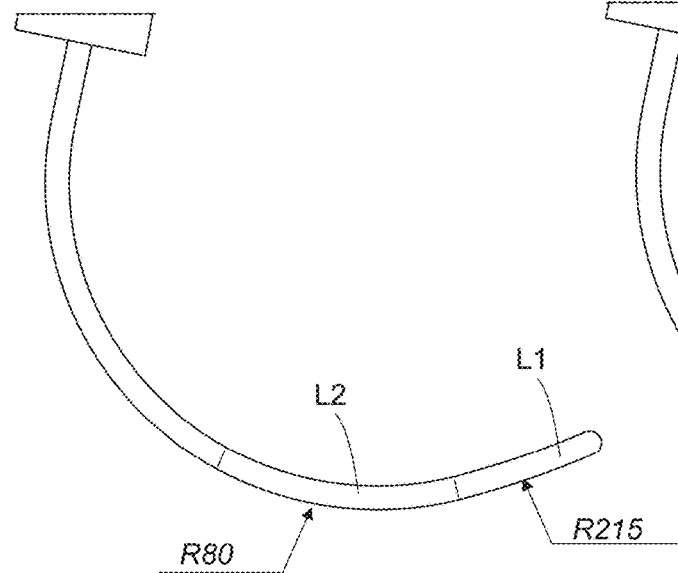
FIG. 30-33 illustrate various bend configurations of the third embodiment of a bendable tip part seen in FIG. 29.

In FIG. 30 none of the first string-operating member and the second string-operating member are operated and the bendable tip part 6' is in its relaxed condition substantially defined by the shape and curvature initially given to the third embodiment of a tip-shaping member 5'''. In the present exemplary configuration, the curvature of the distal length L1 has a radius of 215 mm and the curvature of the proximal length L2 has a radius of 80 mm.

Figure 31:
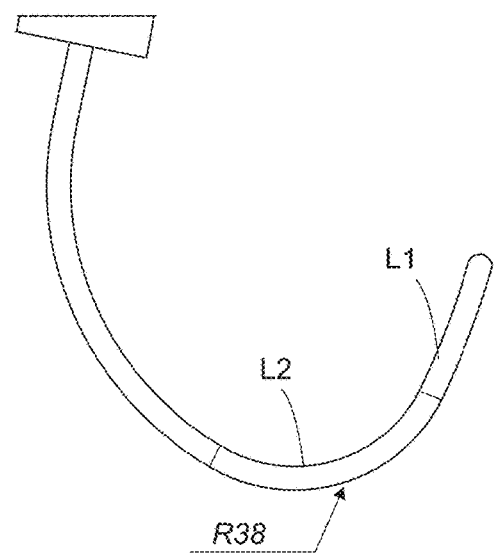

In the configuration shown in FIG. 31 the first string-operating member, which is connected to the first string member 10, has been fully actuated to turn the free distal tip 97' upwards by curving the proximal length L2. The second string-operating member, which is connected to the second string member 11, has not been actuated and the distal length L1 remains substantially straight or keeps the radius of curvature of the configuration of FIG. 30. The radius of the proximal length L2 is reduced substantially from 215 mm to 38 mm.

Figure 32:
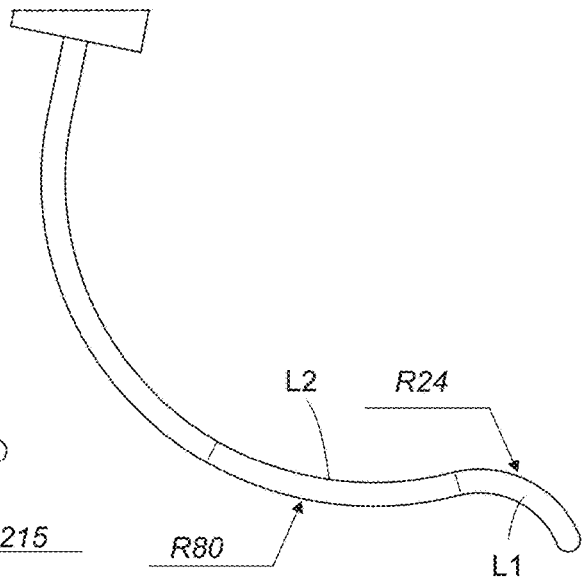

In the configuration shown in FIG. 32 the first string-operating member is not actuated and the curvature of the proximal length L2 is substantially the same as in the configuration seen in FIG. 30. The second string-operating member is now fully actuated and the distal length L1 had been curved to move the free distal tip 97' downwards to achieve a radius of 24 mm.

Figure 33:
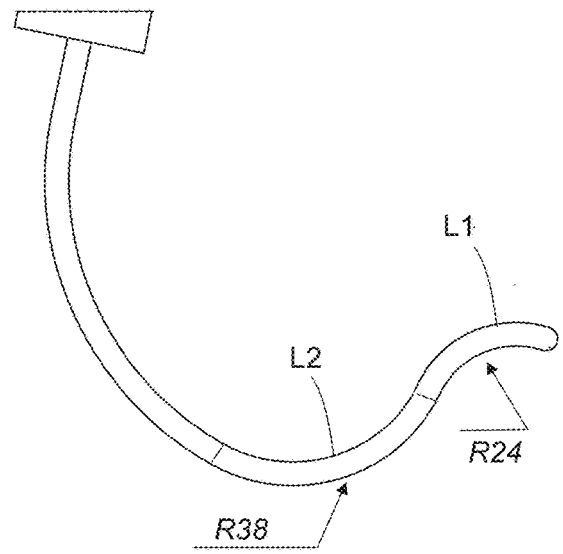

In the situation shown in FIG. 33 both the first string-operating member and the second string-operating member have been fully actuated whereby the proximal length L2 is curved at a radius of 80 mm and the distal length L1 is curved to a radius of 24 mm.

By reducing the actuation force on the string-operating members any intermediate and arbitrary configuration between the configurations seen in FIGS. 30-33 can be provided to the bendable distal tip part.

Figure 34:
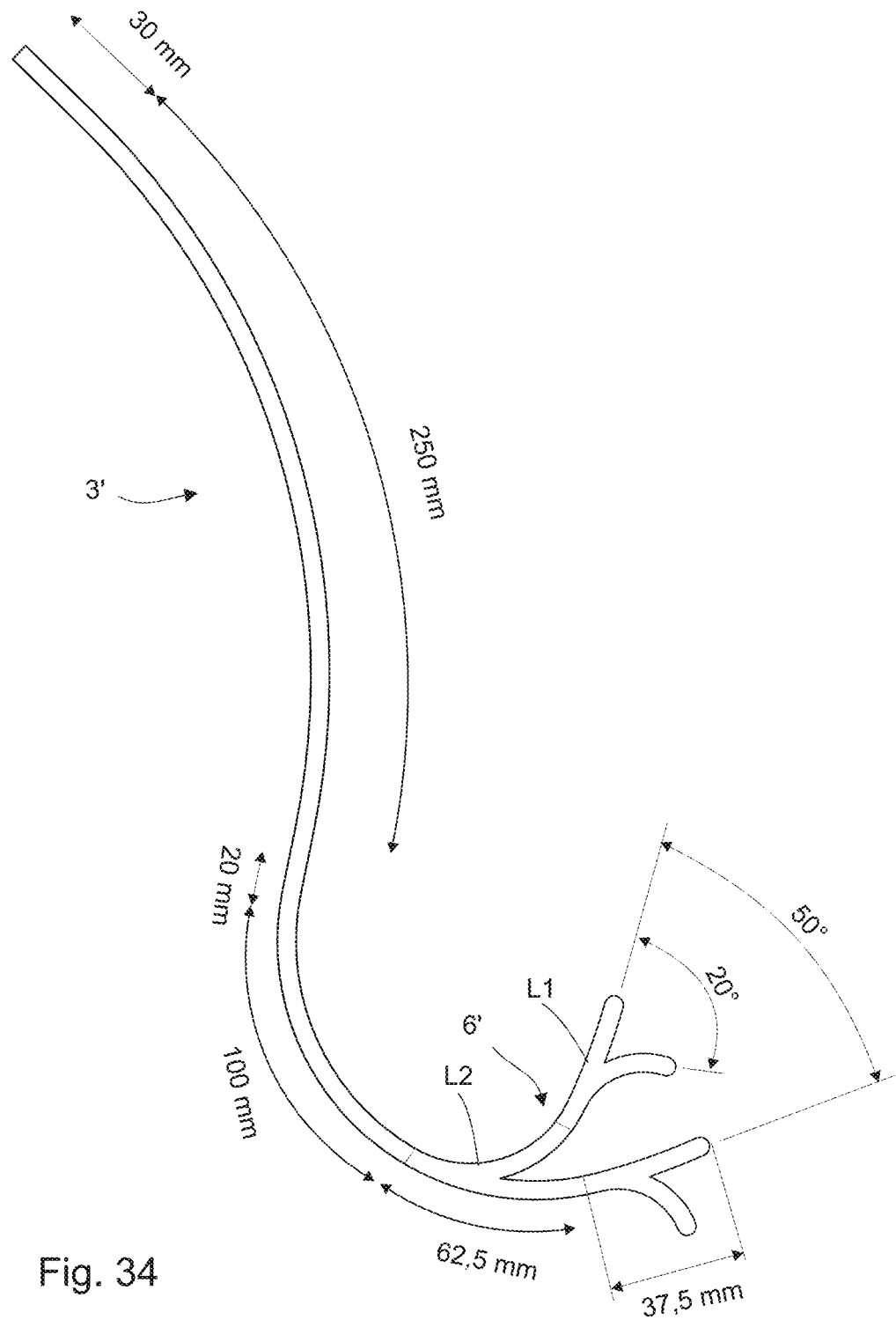
FIG. 34 illustrates, in a combined view, the curvatures seen in FIGS. 30-33 of the bendable tip part in relation to the curvature of the elongate guide member.

FIG. 34 illustrates, in a combined view, all curvatures seen in FIGS. 30-33 of the bendable tip part 6' which is used with a second embodiment of a stylet part 3' having a proximal stylet part curving opposite the curvature of at least the proximal length L2 of the bendable distal tip part 6'.

Figure 35:
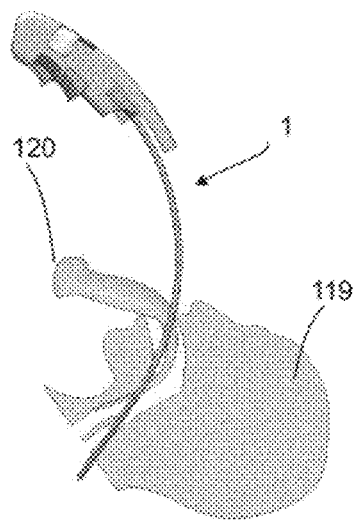
FIG. 35 illustrates the configuration of the first embodiment of an endotracheal tube-inserting device in relaxed configuration next to a patient to be intubated, FIG. 36 illustrate the above configuration of the second embodiment of an endotracheal tube-inserting device 1' in relaxed configuration next to a patient to be intubated.
Figure 36:
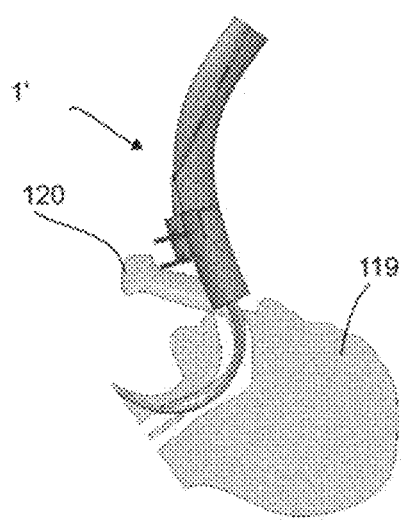

FIG. 35 and FIG. 36 illustrate the above described principles of curvatures and of the configuration of the first embodiment of an endotracheal tube-inserting device 1 and the second embodiment of an endotracheal tube-inserting device 1' in relaxed configuration next to a patient 119 to be intubated in an intubation procedure monitored using a video laryngoscope 120. The endotracheal tube-inserting device 1,1' has not been put in place inside trachea yet in any of FIG. 36 or FIG. 37.

Figure 37:
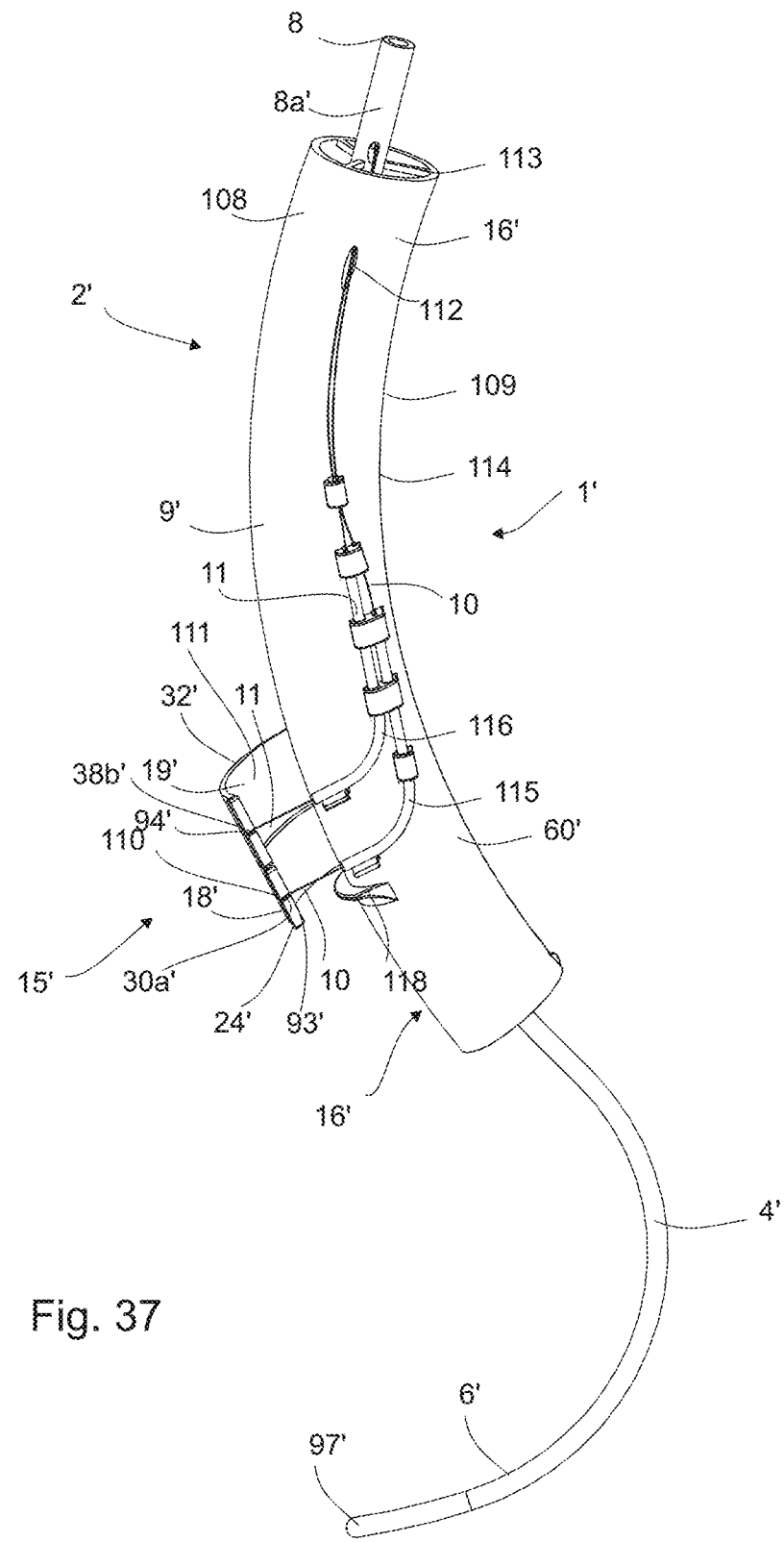
FIGS. 37 and 38 are perspective views of a second embodiment of an endotracheal tube-inserting device of the present invention seen from different sides.
Figure 38:
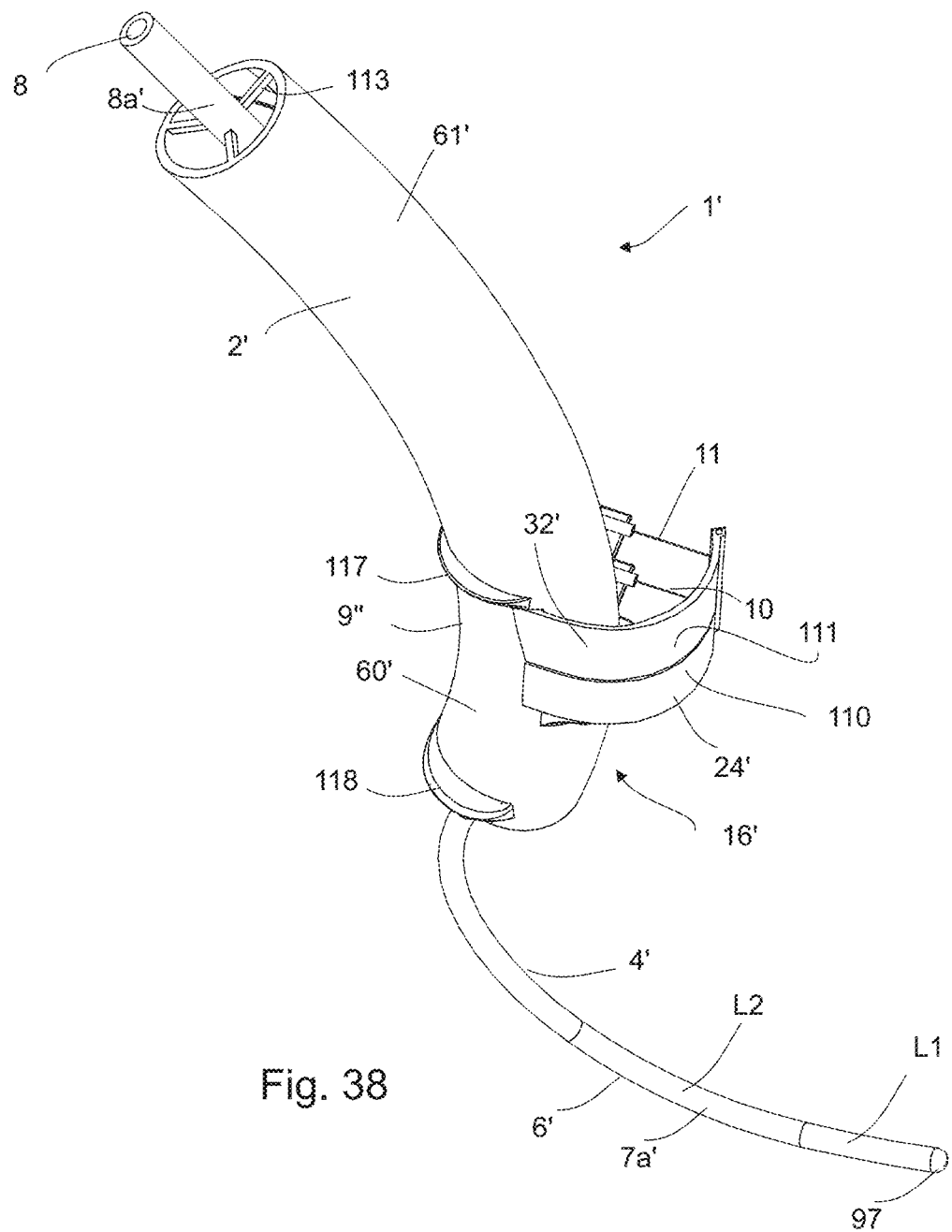

FIG. 37 and FIG. 38 are perspective views of a second embodiment of an endotracheal tube-inserting device 1' of the present invention seen from different sides. The second embodiment of an endotracheal tube-inserting device 1' may utilize any of the bendable tip parts 6,6' and the same or different mechanism as the first embodiment of an endotracheal tube-inserting device 1 to eject the endotracheal tube 86 off the stylet part 3'.

The second embodiment of an endotracheal tube-inserting device 1' mainly differs from the first embodiment of an endotracheal tube-inserting device 1 in the configuration of the housing 9' of the handle part 2', the configuration and position of the string-operating members 18',19' and thus the paths of the string members 10,11, and by the configuration and position of the first actuator 24' and the second actuator 32'. For like parts or similar parts same reference numerals are used and only different features are specifically described.

The housing 9' is a curved tubular body 108 delimited by an exterior tubular wall 109 within which the proximal stylet end part 8a' is at least partly located. The elongate guide member 4' has, using the orientation of FIG. 25, an S-shape, thus the distal stylet end part 7a' and the proximal stylet end part 8a' curves in opposite directions. The housing 9' follows the curvature of at least a length of the proximal stylet end part 8a' and the pre-shaped bendable tip part 6' in its relaxed condition continues to curve in extension of the distal stylet end part 7a'. This configuration of curvatures avails the operator of the endotracheal tube-inserting device with good working posture and good working conditions to the benefit of the patient, and the intubation can be done carefully and considerate. The second embodiment of an endotracheal tube-inserting device 1' has the handle part 2' to bend backwards thereby providing for good clearance to the patient when inserting the bendable tip part 6' via the mouth into trachea while also preserving good control of the device 1'.

The proximal housing end 61' is in FIG. 37 and FIG. 38 shown open-ended to illustrate that the first string member 10 and the second string member 11 pass inside the hollow elongate stylet part 3' close to the proximal stylet end 8' of the proximal stylet end part 8a', whereas the distal housing end 60' allows exit of the stylet part 3'. The first string member 10 and the second string member 11 may enter the housing 9' and pass over various guide means (not shown) to avoid kinking of said string members 10,11 and to confer for an unobstructed and a smooth pulling and relaxing of said string members 10,11 upon operating the first actuator 24' of the first string-operating member 18' and the second actuator 32' of the second string-operating member 19'.

The first actuator 24' of the first string-operating member 18' is constituted by a first curved flap 110 and the second actuator 32' of the second string-operating member 19' is constituted by a second curved flap 111. The curved flaps 110,111 constitute the buttons, which the operator uses to confer a desired curvature and shape to the distal tip part 6' during intubating a patient 119.

As seen in FIGS. 37 and 38 the first string member 10 has a first proximal string end 30a' secured to the first curved flap 110 and an opposite first distal string end 30b' secured at a first string-securing location 93' at the bendable tip part 6'. The first string member 10 runs from the bendable tip part 6' through the stylet part 3' out of the proximal stylet end 8' and out of an exit 112 in the exterior tubular wall 109 at a proximal housing end 61' of the housing 9'. From the exit 112 the first string member 10 continues along the exterior face 114 of the exterior tubular wall 109 guided inside a first guide tube 115 on said exterior tubular wall 109 for having the first proximal string end 30a' securely and operatively connected to the first curved flap 110.

In a similar manner the second string member 11 has a second proximal string end 38a' connected to the second curved flap 111 and an opposite second distal string end 38b' secured at a second string-securing location 94' at the bendable tip part 6'. The second string member 11 runs from the bendable tip part 6' through the stylet part 3' out of the proximal stylet end 8' and out of the exit 112 in the exterior tubular wall 109 at the proximal housing end 61' of the housing 9'. From the exit 112 the second string member 11 continues along the exterior face 114 of the exterior tubular wall 109 guided inside a second guide tube 116 on the exterior tubular wall 109 for having the second proximal string end 38a' securely and operatively connected to the second curved flap 111.

The proximal stylet end part 8a' may be kept fixed, optionally centered inside the lumen of the tubular body 109 at the proximal housing end 61' by means of a centering body 113, which in the exemplary second embodiment of an endotracheal tube-inserting device 1' is reinforcing ribs.

The curved flaps 110,111 are hinged to the exterior wall 109 of the tubular body 108 in a manner that allow the curved flaps 110,111 to be released from a forced position close to the tubular exterior wall 109 by an elastic force and jump back to a released and relaxed position farther away from said exterior tubular wall 109. Thus the curved flaps 110,111 are hinged to the tubular body 108 in manner that provide them with a certain degree of springiness and substantial spring-property.

In the second embodiment of an endotracheal tube-inserting device 1' seen in FIG. 37 and FIG. 38 the first guide tube 115 and the second guide tube 116 are arranged outside the tubular body 109. In an alternative embodiment said guide tubes 115,116 can be arranged on the interior side of the tubular body 109, in which case the exit 112 does not exist.

Instead of being curved flaps the actuators of the string-operating members can be two rocker arms to which the string members have been secured, in same, similar or different manners as described for the first embodiment of an endotracheal tube-inserting device 1 or second embodiment of an endotracheal tube-inserting device 1'.

Opposite the upper housing end 61' of the housing 9', said housing 9' has a lower housing end 60' where the stylet part 3' exit the housing 9'. The exterior tubular wall 109 of the lower part 9" of the housing 9' has finger location means 117,118 on one or both of the sides of the curved flaps 110,111 farthest from each other, thus the side of the curved flaps 110,111 not immediate adjacent each other. The finger location means 117,118 helps the operator to grasp around the tubular body 108 in the correct manner for use of the endotracheal tube-inserting device 1' to operate the actuators 24'32'.

An endotracheal tube 86 can be mounted on and secured to the stylet part 3' as described for the first embodiment of an endotracheal tube-inserting device 1, and the endotracheal tube-inserting device 1' can also have a mechanism to eject the endotracheal tube off the stylet part 3'.

FIGS. 39-43 illustrate a soft flexible free distal tip 97,97' of any of the embodiment of bendable tip parts 6,6' upon being inserted into the endotracheal tube 86 via the endotracheal tube 86's airway connector 87*b*.

In the illustrated exemplary embodiment of a flexible free distal tip 97,97', said flexible free distal tip 97,97' has a soft rounded end 121 that deforms and adapt shape when pressed towards an obstacle.

If e.g. the flexible free distal tip 97,97' is pushed with a force towards and inside an entry section 122 of an airway connector 87*b* that has an interior radius larger than the exterior radius of the relaxed flexible free distal tip 97,97' towards a smaller radius at the exit section 123, the flexible free distal tip 97,97' deforms to a larger radius at the point of contact at the transition between entry section 122 and exit section 123. The contact area of the flexible free distal tip 97,97' against the interior surface of the airway connector 87*b* becomes enlarged as illustrated in FIG. 40. During further introduction into the endotracheal tube 86 the flexible free distal tip 97,97' conforms again to the interior diameter of said endotracheal tube 86 by being slightly compressed and thereby made longer, as seen in FIG. 41.

The bendable tip part 6,6' is moved further inside the endotracheal tube 86 past the inflatable cuff 124 and out of the ventilation end opening 125, as illustrated in FIG. 42, to serve its purpose of being the front object when guiding the endotracheal tube 86 into its ventilation position inside trachea using the endotracheal tube-inserting device 1,1'. The soft and resilient flexible free distal tip 97,97' distributes the contact force to the tissue 126, as exemplified by the box 126, onto a large area, as seen in FIGS. 43*a*-43*c*, which lower the risk of damage to the tissue. The flexible free distal tip 97,97' may be chosen so that it floats out at a low contact force, but also allows passage of the endotracheal tube, by collapsing to a smaller diameter when compressed by entering said endotracheal tube 8. These properties of the flexible free distal tip 97,97' can be given to said flexible free distal tip 97,97' by e.g. selecting shape, and choice of material and degree of wall thickness.

Emphasis is made that although the first lever body and the second lever body of the first embodiment of an endotracheal tube-inserting device are described as a triangle with a center hole, other lever body designs are within the scope of the present invention. The triangular structure can e.g. be replaced by a solid triangular plate, in which case the edge areas of the triangle are equivalent to the arms of the triangular structure and is utilized and functions in a similar manner. Other shapes than triangular, such as oval, polygonal and circular are also possible within the scope of the present invention. The outline of the first actuator and of the second actuator is curved, preferably having similar curvature as defined by the pivot radius.

In the above first embodiment of an endotracheal tube-inserting device the first lever body and the second lever body where both designed with pivotable lever arms. Alternative embodiments of actuators may include alternatives to such lever bodies. Thus axial displacing the first distal securing location and the second distal securing location may in the alternative be provided by connecting the first proximal string end of the corresponding first string member and the second proximal string end of the corresponding second proximal string member, respectively, to e.g. a toggle mechanism, an articulated mechanism, a rotating mechanism, or even a gear transmission. These alternatives are however more space-demanding, which makes the handle part larger and less handy. These alternatives are also more complex structures that make the endotracheal tube-inserting device more expensive and more vulnerable to malfunction.

The above second embodiment of an endotracheal tube-inserting device can be configured with the actuator flaps positioned for use by right hand or left hand and due to the actuator flaps being positioned on the side of the housing the index finger will inherently be placed on the second flap and the middle finger be placed on the first body while the other fingers grasp around the housing, so that the thumb can be used to operate the third actuator of the tube ejecting mechanism.

Although the above first embodiment of an endotracheal tube-inserting device has actuators protruding from a short edge towards the center of curvature of the stylet part the third actuator is reachable by the thumb from a side of the housing and usable by right-handed or left-handed operators depending on from which side the third actuator protrude.

Within the scope of the present invention a string member can e.g. be any kind of elongate thin pulling means that can fit inside the elongate guide member and having a sufficient strength to pull the tip-shaping member without accidentally rupturing when tensioned. Suitable string members include but are not limited to a metal wire, a nylon wire, e.g. a fish line, or similar means that can tension the tip-shaping member in response to application of a force onto a string-operating member.

Examples of tip-shaping members adapted to be operatively accommodated inside the tubular cover include but are not limited to one or more flat springs, e.g. a thin strip of spring steel, or a tension spring, e.g. a coiled spring, or combinations of those.

The tip-shaping member preferably has springiness that provides for the backstroke on the string-operating members.

Above the first embodiment of the endotracheal tube-inserting device of the present invention includes a suspension body to amongst other suspend the string-operating members, and control the orientation and pivoting of said string-operating members. For example, the suspension body is designed and arranged to restrict and stop downwards movement of an actuator. The suspension body further facilitates the correct functional and mechanical assembling of the relevant components of the mechanism to bend the bendable tip part, and the relevant components of the mechanism to eject the endotracheal tube off the stylet part.

In an alternative first embodiment the endotracheal tube-inserting device may however be designed without suspension body and the string-operating members be pivotable suspended directly to e.g. a pin crosswise the shell part of the housing. Stops for preventing the actuators from been depressed too far into the housing can simply protrude from a shell part inside the space delimited by said shell parts.

The second embodiment of an endotracheal tube-inserting device is yet an alternative embodiment that can have flaps or rockers as actuators.

The present invention has a minimum of structural components, which makes productions costs low and the risk that a structural components fails is at an absolute minimum.

Moreover, since the structural components to be accommodated inside the housing are small and few, and can be combined at minimum space, the handle part of the endotracheal tube-inserting device of the present invention has a very ergonomic design.

The elongate guide member can advantageously be made of metal, such as malleable aluminum, which allows the stylet part to be easily adapted to any desired anatomy and use, but plastic is an alternative.

Accordingly, the advantages of the endotracheal tube-inserting device and endotracheal procedure and methods described herein further include, without limitation, the ability to control the shape of the distal tip part of an endotracheal tube, the ability to respond to unique anatomical differences in tracheal location and shape. The entire endotracheal tube-inserting device may be disposable in its entirety, or the stylet part may be a separate disposable unit for one time use and the handle part be for reuse. So the stylet part can be a disposable stylet part while continuing use of the handle part is within the scope of the present invention.

So the endotracheal tube-inserting device can be a kit of parts, which parts e.g. may include a reusable handle part and a selection of stylet parts and endotracheal tubes to go with the stylet part. Alternative compositions of the kits of parts are within the scope of the present invention.

Emphasis is made that the first embodiment of an endotracheal tube-inserting device 2 and the second embodiment of an endotracheal tube-inserting device 2' can implement and combine any of the bendable tip parts 6,6' shown and described in relation to FIGS. 21-34, as well as the various options for actuation means, tip part operating means, handle parts and housings described above can be used and mixed and combined to the extent desired and possible thereby arriving to even further embodiments within the scope of the appended claims.

Within the scope of the present invention the curvatures of the proximal stylet end part, the distal stylet end part, and the pre-shaped distal end part can curve as any of the endotracheal tube-inserting devices 1. Similarly, the first embodiment of an endotracheal tube-inserting device 1 can have the curvatures corresponding to the curvatures of the proximal stylet end part, the distal stylet end part, and the pre-shaped distal end part of the second embodiment of an endotracheal tube-inserting device 1'.

Combinations, modifications of and deviations from such curvatures are within the scope of the present invention.

The invention claimed is:

1. An endotracheal tube-inserting device (1;1') comprising a stylet part (3;3') and a handle part (2;2') for operating the stylet part (3;3'),
the stylet part (3;3') has a proximal stylet end part (8a;8a') with a proximal stylet end (8;8') and an opposite distal stylet end part (7a;7a') with a distal stylet end (7;7'),
at least a part of the proximal stylet end part (8a;8a') is situated at or inside the handle part (2;2'), and the distal stylet end (7;7') has an extension in the form of a bendable tip part (6;6') with a free distal tip (97;97') at the free end of the bendable tip part (6;6'),
a tip part operating member (16;16') includes at least a first string member (10) and a second string member (11) arranged along the length of at least a length of the stylet part (3;3'), and
the handle part (2;2') has an actuator (15;15') for operating at least the tip part operating member (16;16'),
wherein the first string member (10) has a first proximal string end (30a;30a') connected to a first string-operating member (18;18') of the actuator (15;15') and an opposite first distal string end (30b;30b') secured at a first string-securing location (93;93') at the bendable tip part (6;6'),
the second string member (11) has a second proximal string end (38a;38a') connected to a second string-operating member (19;19') of the actuator (15;15') and an opposite second distal string end (38b;38b') secured at a second string-securing location (94;94') at the bendable tip part (6;6'), which second string-securing location (94;94') is different from the first string-securing location (93;93'),
the stylet part (3;3') comprises an elongate guide member (4;4') that extends into the bendable tip part (6;6'), which elongate guide member (4;4') and bendable tip part (6;6') lengthwise encases or supports at least a part of the first string member (10) and at least a part of the second string member (11),
the bendable tip part (6;6') includes a tip-shaping member (5;5';5'''), and at least a distal part of said tip-shaping member (5;5';5''') is accommodated inside a flexible tubular cover (12),
the first string-securing location (93;93') and the second string-securing location (94;94') are situated lengthwise offset at the bendable tip part (6;6'), and
the first distal string end (30b;30b') and the second distal string end (38b;38b') are individually attached to the tip-shaping member (5;5';5'''),
wherein the endotracheal tube-inserting device (1) further comprises an endotracheal tube.

2. The endotracheal tube-inserting device (1;1') according to claim 1, wherein the tip-shaping member (5;5';5''') returns to a relaxed start position when the actuator (15;15') is relaxed.

3. The endotracheal tube-inserting device (1;1') according to claim 1, wherein the elongate guide member (4;4') is hollow.

4. The endotracheal tube-inserting device (1;1') according to claim 1, wherein the tip-shaping member (5;5';5''') has a first end (95;95') and an opposite second end (96;96').

5. The endotracheal tube-inserting device (1;1') according to claim 4, wherein a length of the tip-shaping member (5;5';5''') extending from the second end (96;96') extends inside the elongate guide member (4;4').

6. The endotracheal tube-inserting device (1;1') according to claim 1, wherein the tip-shaping member (5;5';5''') includes at least one elongate spring member (5'').

7. The endotracheal tube-inserting device (1;1') according to claim 1, wherein the tip-shaping member (5;5';5''') includes at least two elongate plate springs (5a) arranged at least partly overlapping each other, or the tip-shaping member (5;5';5''') is a solid member having different thicknesses along sections of its length.

8. The endotracheal tube-inserting device (1;1') according to claim 1, wherein the tip-shaping member (5;5';5''') includes a spring member (5'') of spring steel or a plastic material having similar bending properties as spring steel.

9. The endotracheal tube-inserting device (1;1') according to claim 6, wherein the tip-shaping member (5''') includes at least one pulley wheel (100;103;104;105) having an axle fixed to the at least one elongate spring member (5'') at a string-securing location or fixed to the distal stylet end (7) of the elongate guide member (4;4').

10. The endotracheal tube-inserting device (1;1') according to claim 9, wherein the at least one pulley wheel (100;103;104;105) comprises a distal pulley wheel (100) provided on a first side of the at least one spring member (5'') at a first pulley wheel location (W1) at the free distal tip (97;97') at the end of the bendable tip part (6;6'), a proximal pulley wheel (103) provided on a second side of the at least one spring member (5'') opposite the first side at a second pulley wheel location (P2) spaced apart from the first pulley wheel location (W1), a distal intermediate pulley wheel (104) and a proximal intermediate pulley wheel (105) provided adjacent each other on opposite sides of the at least one spring member (5'') at an intermediate pulley wheel location (W3) between the first pulley wheel location (W1) and the second pulley wheel location (P2), which distal intermediate pulley wheel (104) is provided on the first side of the at least one spring member (5") and the proximal intermediate pulley wheel (105) is provided on the second side of the at least one spring member (5").

11. The endotracheal tube-inserting device (1;1') according to claim 3, wherein at least a part of the first string member (10) and at least a part of the second string member (11) runs inside a common lumen of the elongate guide member (4;4').

12. The endotracheal tube-inserting device (1;1') according to claim 1, wherein at least a part of the first string member (10) and at least a part of the second string member (11) runs alongside the elongate guide member (4;4'), and the flexible tubular cover (12) is extended to cover said string members.

13. The endotracheal tube-inserting device (1;1') according to claim 1, wherein an exterior face of the tubular cover (12) has a coefficient of friction that is lower than the coefficient of friction of an endotracheal tube (86) to be mounted on the device.

14. The endotracheal tube-inserting device (1;1') according to claim 1, wherein the stylet part (3;3') has a first center of curvature above said stylet part (3;3'), and at least a proximal length (L2) of the bendable tip part (6;6') has a second center of curvature above said bendable tip part (6;6').

15. The endotracheal tube-inserting device (1;1') according to claim 1, wherein the stylet part (3;3') has a first center of curvature below said stylet part (3;3') and at least a proximal length of the bendable tip part (6;6') has a second center of curvature above said bendable tip part (6;6').

16. The endotracheal tube-inserting device (1;1') according to claim 1, wherein the handle part (2;2') comprises a housing (9;9').

17. The endotracheal tube-inserting device (1;1') according to claim 16, wherein the housing (9;9') curves the same way as the hollow guide member (4;4').

18. The endotracheal tube-inserting device (1;1') according to claim 16, wherein the housing (9;9') is a curved tubular body having a circumferential exterior wall (109).

19. The endotracheal tube-inserting device (1;1') according to claim 1, wherein the first string-securing location (93;93') and the second string-securing location (94;94') are situated laterally offset at the bendable tip part (6;6').

20. The endotracheal tube-inserting device (1) according to claim 16, wherein the first string-operating member (18) of the actuator (15) includes a first lever body (20) arranged about a first pivot axis (P1), and the second string-operating member (19) of the actuator (5) includes a second lever body (22) pivotably arranged about a second pivot axis (P2),
said first lever body (20) has at least one first actuator lever arm (23) extending from the first pivot axis (P1) to a first actuator (24), and at least one opposite first string-operating lever arm (25) at which the first proximal string end (30a) is operatively connected to change the position of the first distal string end (30b) relative to at least the distal stylet end (7) in response to actuating the first actuator (24),
said second lever body (22) has at least one second actuator lever arm (31) extending from the second pivot axis to a second actuator (32), and at least one opposite second string-operating lever arm (33) to which the second proximal string end (38a) is operatively connected to change the position of the second distal string end (38b) relative to at least the distal stylet end (7) in response to actuating the second actuator (32).

21. The endotracheal tube-inserting device (1) according to claim 20, wherein the housing accommodates at least the first lever body (20) and the second lever body (22), which housing (9) has a first opening (63) for making the first actuator (24) accessible to pivot the first lever body (20) from outside the housing (9), and a second opening (64) for making the second actuator (32) accessible to pivot the second lever body (22) from outside the housing (9).

22. The endotracheal tube-inserting device (1) according to claim 20, wherein the first lever body (20) is pivotably suspended to move a first string-securing member (29) of the housing (9) and the second lever body (22) is pivotably suspended to move a second string-securing member (37) of the housing (9), and wherein the first string-securing member (29) is arranged spaced from the first pivot axis (P1), and the second string-securing member (37) is arranged spaced from the second pivot axis (P2).

23. The endotracheal tube-inserting device (1) according to claim 20, wherein the endotracheal tube-inserting device (1) further includes
a suspension body (17) inside the housing (9) and being configured with the first pivot axis (P1) and the second pivot axis (P2) for pivotally suspending of the first lever body (20) and the second lever body (22), respectively,
the first proximal string end (30a) is operatively connected to the end of the first string-operating lever arm (25) opposite the first pivot axis (P1) to displace the first string member (10) along the elongate guide member (4),
the second proximal string end (38a) is operatively connected to the end of the second string-operating lever arm (33) opposite the second pivot axis (P2) to displace the second string member (11) along the elongate guide member (4),
and wherein
the first string-securing member (29) and the second string-securing member (37) are arranged below the suspension body (17) opposite the respective first actuator (24) and second actuator (32).

24. The endotracheal tube-inserting device (1) according to claim 20, wherein
the first lever body (20) is a first bifurcated lever body having opposite first legs (L1a;L1b) joined by the first actuator (24), which opposite first legs (L1a;L1b) extend from the first actuator (24) into opposite first actuator lever arm (23) that extend further via the first pivot axis (P1) into opposite first string-operating lever arms (25), and
the second lever body (22) is a second bifurcated lever body having opposite second legs (L2a;L2b) joined by the second actuator (32), which opposite second legs (L2a;L2b) extend from the second actuator (32) into opposite second actuator lever arms that (31) extend further via the second pivot axis (P2) into opposite second string-operating lever arms (33).

25. The endotracheal tube-inserting device (1) according to claim 24, wherein the suspension body (17) is inserted between the opposite first legs (L1a;L1b) of the first bifurcated lever body (20) and between the opposite second legs (L2a;L2b) of the second bifurcated lever body (22).

26. The endotracheal tube-inserting device (1') according to claim 20, wherein the housing (9;9') is a curved tubular body having a circumferential exterior wall (109), and wherein the first actuator (24') of the first string-operating member (18') and the second actuator (32') of the second string-operating member (19') are hinged to the circumferential exterior wall (109) of the curved tubular body (108) of the housing (5') to pivot between a relaxed position wherein any of the first actuator (24') and the second actuator (32') protrude spaced from the circumferential exterior wall (109) and an actuated position wherein the second actuator (32') are closer to the circumferential exterior wall (109) than in the relaxed position.

27. The endotracheal tube-inserting device (1') according to claim 20, wherein the first actuator (24') and the second actuator (32') are flaps (110;111).

28. The endotracheal tube-inserting device (1') according to claim 27, wherein the flap (110;111) is provided by a cross-sectional segment of the circumferential exterior wall (109) or the flap (110;111) is a separate part pivotably secured to the circumferential exterior wall (109).

29. The endotracheal tube-inserting device (1;1') according to claim 3, wherein the handle part (2;2') comprises a housing (9;9'), and wherein the proximal stylet end of the hollow guide member (4;4') is located inside the housing.

30. The endotracheal tube-inserting device (1;1') according to claim 1, wherein the free distal tip (97;97') at the end of the distal tip part (6;6') is soft and flexible.

31. The endotracheal tube-inserting device (1;1') according to claim 1, wherein the endotracheal tube (68) is sheathed on the stylet part (3;3').

32. The endotracheal tube-inserting device (1;1') according to claim 1, wherein a conical tube connector (83) is provided at the proximal stylet end (8;8') of the elongate guide member (4;4').

33. The endotracheal tube-inserting device (1;1') according to claim 1, wherein the endotracheal tube-inserting device (1;1') further has a tube ejecting mechanism (65).

34. The endotracheal tube-inserting device (1;1') according to claim 33, wherein the handle part (2;2') comprises a housing (9;9'), and wherein the tube ejecting mechanism (65) comprises a ratchet mechanism (66) comprising a rack part (68) extending along the length of the housing (9;9') and being arranged opposite a wedge part (69) having a tube connector (83) in order to engage the rack part (68).

35. The endotracheal tube-inserting device (1;1') according to claim 34, wherein the rack part (68) has a first stationary rack part (70), a second stationary rack part (71), and a moveable third rack part (72) arranged lengthwise between the first stationary rack part (70) and the second stationary rack part (71), which moveable third rack part (72) has a third actuator (67) arranged to protrude from the housing (9;9'), wherein the moveable third rack part (72) is suspended inside the housing (9;9') by means of a resilient means, and a proximal end (82) of the wedge part (69) is provided with opposite lateral wedge parts (80;81) and a center wedge part (79) located between said lateral wedge parts (80;81).

* * * * *